(12) United States Patent
Lee et al.

(10) Patent No.: US 7,807,762 B2
(45) Date of Patent: *Oct. 5, 2010

(54) CATALYST COMPOSITION COMPRISING GROUP 4 TRANSITION METAL COMPLEXES AND METHOD FOR PREPARING POLYOLEFINS USING THE SAME

(75) Inventors: Choong-Hoon Lee, Daejeon Metropolitan (KR); Eun-Jung Lee, Daejeon Metropolitan (KR); Seung-Whan Jung, Suwon-Si (KR); Jung-A Lee, Gangwon-Do (KR); Bo-Ram Lee, Seoul (KR); Bun-Yeoul Lee, Suwon-Si (KR)

(73) Assignee: LG Chem, Ltd. (KR)

( * ) Notice: Subject to any disclaimer, the term of this patent is extended or adjusted under 35 U.S.C. 154(b) by 39 days.

This patent is subject to a terminal disclaimer.

(21) Appl. No.: 12/087,216

(22) PCT Filed: Dec. 29, 2006

(86) PCT No.: PCT/KR2006/005907

§ 371 (c)(1),
(2), (4) Date: Jun. 25, 2008

(87) PCT Pub. No.: WO2007/078133

PCT Pub. Date: Jul. 12, 2007

(65) Prior Publication Data

US 2009/0005525 A1    Jan. 1, 2009

(30) Foreign Application Priority Data

Dec. 30, 2005 (KR) .................. 10-2005-0135900
Jul. 18, 2006 (KR) .................. 10-2006-0067117

(51) Int. Cl.
*C08F 4/64* (2006.01)
*C08F 4/6592* (2006.01)
*B01J 31/22* (2006.01)

(52) U.S. Cl. .............. 526/116; 502/103; 502/152; 502/155; 526/113; 526/160; 526/161; 526/165; 526/943

(58) Field of Classification Search ............. 502/103, 502/152, 155; 526/160, 161, 165, 116, 348, 526/943

See application file for complete search history.

(56) References Cited

U.S. PATENT DOCUMENTS

| | | | |
|---|---|---|---|
| 5,064,802 A | 11/1991 | Stevens et al. | |
| 5,399,635 A | 3/1995 | Neithamer et al. | |
| 5,453,410 A | 9/1995 | Kolthammer et al. | |
| 6,090,739 A | 7/2000 | Riedel et al. | |
| 6,153,776 A | 11/2000 | Patton et al. | |
| 6,228,790 B1 | 5/2001 | Ting et al. | |
| 6,235,917 B1 | 5/2001 | Graf et al. | |
| 6,548,686 B2 | 4/2003 | Nboka et al. | |
| 6,617,466 B1 | 9/2003 | Canich | |
| 6,636,597 B2 | 10/2003 | Porter et al. | |
| 6,686,488 B2 | 2/2004 | Wilson et al. | |
| 6,825,369 B1 | 11/2004 | Stevens et al. | |
| 7,517,940 B2 | 4/2009 | Lee et al. | |
| 2003/0191334 A1 | 10/2003 | Schottek et al. | |

FOREIGN PATENT DOCUMENTS

| | | | |
|---|---|---|---|
| EP | 0311899 A2 | 4/1989 | |
| EP | 0416815 A2 | 3/1991 | |
| EP | 0418044 A2 | 3/1991 | |
| EP | 0520732 A1 | 12/1992 | |
| JP | 08-325283 | * 12/1996 | |
| WO | 2007007992 A1 | 1/2007 | |

OTHER PUBLICATIONS

Cho et al., "o-Phenylene-Bridged Cp/Amino Titanium Complexes for Ethylene/1-Hexene Copolymerizations", Organometallics, vol. 25, No. 9, pp. 2133-2134, 2006.
Gibson et al., "Advances in Non-Metallocene Olefin Polymerization Catalysis", Chem. Rev. vol. 103, pp. 283-315, 2003.
Chen et al., "A Novel Phenolate"Constrained Geometry" Catalyst System. Efficient Synthesis, Structural Characterization, and α-Olefin Polymerization Catalysis", Organometallics, vol. 16, pp. 5958-5963, 1997.
Zhang et al., "Constrained Geometry Tetramethylcyclopentadienly-phenoxytitanium Dichlorides: Template Synthesis, Structures, and Catalytic Properties for Ethylene Polymerization" Organometallics, vol. 23, pp. 540-546, 2004.
Turner et al., "Facile resolution of constrained geometry indenyl-phenoxide ligation", Chem. Commun. pp. 1034-1035, 2003.
Christie et al., "Novel Routes to Bidentate Cyclopentadienyl-Alkoxide Complexes of Titanium: Synthesis of ($n^5$-o-$C_5R^1{}_4CHR^2CH_2CR^3R^4O$)$TiCl_2$", Organometallics, vol. 18, pp. 348-359, 1999.
Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group" Organometallics, vol. 17, pp. 1652-1654, 1998.
Rau et al., "Synthesis and application in high-pressure in high-pressure polymerization of a titanium complex with a linked cyclopentadienyl-phenoxide ligand", Journal of Organometallic Chemistry, vol. 608, pp. 71-75, 2000.
Guo et al., "Bimetallic Catalysis for Styrene Homopolymerization and Ethylene-Styrene Copolymerization. Exceptional Comonomer Selectivity and Insertion Regiochemistry", J. Am. Chem. Soc., vol. 126, pp. 6542-6543, 2004.

(Continued)

*Primary Examiner*—Caixia Lu
(74) *Attorney, Agent, or Firm*—Lerner, David, Littenberg, Krumholz & Mentlik, LLP

(57) ABSTRACT

The present invention relates to a catalyst composition comprising a novel structure of a Group 4 transition metal compound, to a method for preparing the same, and to a method for preparing a polyolefin using the catalyst composition. The method for preparing a polyolefin according to the present invention can be used for preparing a polyolefin having a high molecular weight and high copolymerizability with a high activity even at a high polymerization temperature and for preparing a polyolefin having a double composition distribution.

13 Claims, No Drawings

OTHER PUBLICATIONS

Gomes, et al.; "Ansa-bridged n-cyclopentadienyl imido and amido derivatives of titanium, zirconium, niobium and molybdenum"; Journal ofOrganometallic Chemistry; vol. 541; pp. 121-125; 1997. cited by other.

Anastassiou, et al.; "NMR detection of anions of N-methyl-l-benzazocinide; 1-benzazocindiide, and dibenz[b.g] azocindiide, a family of aromatic charge trans compounds"; Angew, Chem. vol. 94, No. 10; pp. 803-804; 1982. cited by other.

International Search Report dated May 4, 2007 for Application No. PCT/KR2007/000560.

* cited by examiner

CATALYST COMPOSITION COMPRISING GROUP 4 TRANSITION METAL COMPLEXES AND METHOD FOR PREPARING POLYOLEFINS USING THE SAME

TECHNICAL FIELD

The present invention relates to a catalyst composition comprising a novel Group 4 transition metal compound, to a method for preparing the same, and to a method for polymerization of olefin using the catalyst composition. Specifically, the present invention relates to a catalyst composition comprising a novel mononuclear transition metal compound in which a cyclopentadienyl group and an amido or phosphorous group are bridged via a phenylene bridge, or a novel binuclear transition metal compound in which the two bridged mononuclear transition metal compounds are linked via a bridging group located at the phenylene bridge, to a method for preparing the same, and to a method for polymerization of olefin using the catalyst composition.

This application claims priority benefits from Korean Patent Application Nos. 10-2005-0135900 and 10-2006-0067117, filed on Dec. 30, 2005 and Jul. 18, 2006, respectively, the entire contents of which are fully incorporated herein by reference.

BACKGROUND ART

The Dow Chemical Company announced [Me$_2$Si(Me$_4$C$_5$)NtBu]TiCl$_2$ (Constrained-Geometry Catalyst, which will be simply referred to as CGC) in the early 1990's (U.S. Pat. No. 5,064,802), wherein in the copolymerization reaction of ethylene and alpha-olefin, excellent characteristics that the CGC has, as compared with per se known metallocene catalysts can be usually classified into the two categories: (1) it produces a high molecular weight polymer with high activity even at a high polymerization temperature, and (2) it yield very excellent copolymerization of an alpha-olefin having high steric hindrance, such as 1-hexene and 1-octene. In addition, upon polymerization reaction, there have been gradually several characteristics of CGC, and thus extensive studies to synthesize a derivative of CGC for use as a polymerization catalyst have been made in the academic and industrial fields.

As one approach, there have been trials for synthesis of metal compounds to which various bridges and nitrogen substituents instead of silicon bridges are introduced, and polymerization using the same. Some representative examples of recently known metal compounds include the followings (*Chem. Rev.* 2003, 103, 283):

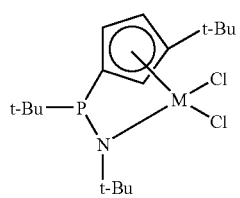

(1)

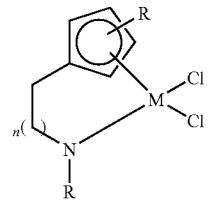

(2)

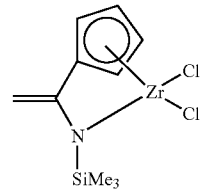

(3)

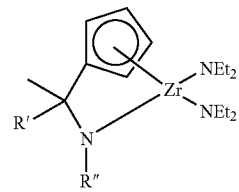

(4)

To the above-listed compounds, a phosphorous bridge (1), an ethylene or propylene bridge (2), a methylidene bridge (3), and a methylene bridge (4) are each introduced, instead of the silicon bridges in the CGC structure. However, when they are used for ethylene polymerization, or copolymerization with an alpha-olefin, they had no excellent results regarding the activity or the copolymerization performances, as compared with CGC.

As another approach, there have trials for synthesis of many compounds comprising an oxido ligand instead of the amido ligand of the CGC, and sometimes polymerization using the same. Examples thereof are summarized as follows:

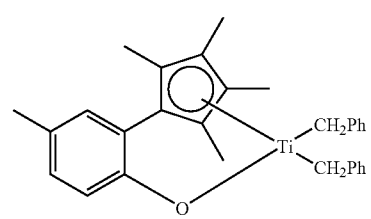

(5)

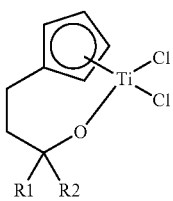

(6)

-continued

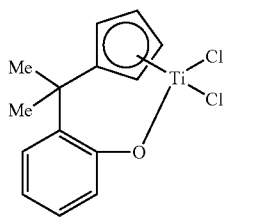

(7)

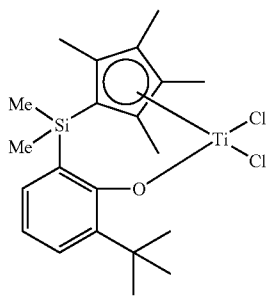

(8)

The compound (5) is characterized in that a Cp derivative and an oxido ligand are bridged via an ortho-phenylene group, as disclosed by T. J. Marks, et al.(*Organometallics* 1997, 16, 5958). Also, a compound having the same bridge and polymerization using the same are disclosed by Mu, et al. (*Organometallics* 2004, 23, 540). Further, an indenyl ligand and an oxido ligand are bridged via the same ortho-phenylene group, as disclosed by Rothwell, et al. (*Chem. Commun.* 2003, 1034). The (6) is characterized in that a cyclopentadienyl ligand and an oxido ligand are bridged through three carbons, as disclosed by Whitby, et al. (*Organometallics* 1999, 18, 348), and these catalysts are reported to exhibit activity on syndiotactic polystyrene polymerization. Further, similar compounds are also reported by Hessen, et al.(*Organometallics* 1998, 17, 1652). The compounds shown in (7) is characterized in that it exhibits activity on ethylene and ethylene/1-hexene copolymerization at a high temperature and a high pressure (210° C., 150 MPa), as disclosed by Rau, et al. (*J. Organomet. Chem.* 2000, 608, 71). Further, synthesis of a catalyst having the similar structure (8), and polymerization using the catalyst at a high temperature and a high pressure were filed in the patent application by Sumitomo Corp. (U.S. Pat. No. 6,548,686).

Recently, a compound having two metal positions was developed, and has been employed as a polymerization catalyst since then. U.S. Pat. No. 6,153,776 describes a binuclear metal compound in which two compounds in the CGC form are bridged via a cyclopentadienyl (Cp) group, an Si bridge, or an N substituent group, and a method for preparing an olefin polymer using the same. Marks, et al., [*J. Am. Chem. Soc.*, 2004, 126, 6542-6543] describes that if a binuclear Ti metal compound in which two compounds in the CGC form are bridged via a —$CH_2CH_2$— group is used for styrene homopolymerization and ethylene/styrene copolymerization reactions, the polymerization activity is more excellent than that of the conventionally used CGC compounds. Further, Marks, et al, describes an example in which a Ti compound and a Zr compound, each in the CGC form, are sequentially bridged to prepare a binuclear Ti/Zr metal compound, and this compound can be used for an ethylene homopolymerization reaction for preparation of polyethylene having a branch, even without comonomers. Accordingly, the above prior arts show that by using a binuclear metal compound for an olefin polymerization reaction, a polyolefin having more excellent activity and novel physical properties can be prepared, as compared with when using the conventionally used single metal compound.

However, in spite of the above trials, only few catalysts are substantially in use for commercial plants. Thus, there is still a need of development of a catalyst having a novel structure, and preparation of a polymer using the same. Particularly, the conventional binuclear catalyst compounds still have structures in the CGC form, and the method for preparing the same is complex and the production yield is low. Therefore, there is still a desire of a binuclear transition metal compound having a novel structure, which is capable of exhibiting a catalytic activity, and a method for simply preparing the same in high yield.

DISCLOSURE OF INVENTION

Technical Problem

It is an object of the present invention to provide a catalyst composition comprising a novel structure of a Group 4 transition metal catalyst, which can be used for preparing a polyolefin having a high molecular weight and high copolymerizability with a high activity even at a high polymerization temperature and for preparing a polyolefin having a double composition distribution, a method for preparing the same, and a method for preparation of polyolefin using the catalyst composition.

Technical Solution

The present invention provides a catalyst composition comprising:

a) at least one transition metal compound selected from the group consisting of a transition metal compound of the following formula 1 and a transition metal compound of the following formula 2; and b) at least one cocatalyst compound selected from the group consisting of the compounds represented by the following formulae 3 to 5:

[Formula 1]

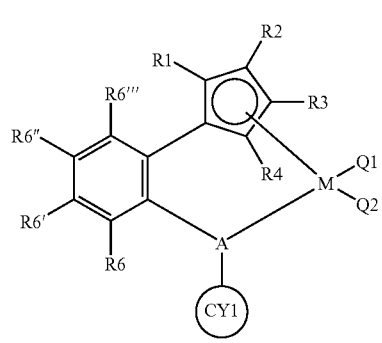

wherein

R1 to R4 are each independently a hydrogen atom; an alkyl radical having 1 to 20 carbon atoms; an aryl radical having 6 to 20 carbon atoms; an alkenyl radical having 2 to 20 carbon atoms; an alkylaryl radical having 7 to 20 carbon atoms; an arylalkyl radical having 7 to 20 carbon atoms radical; or a metalloid radical of a Group 14 metal substituted with hydrocarbyl having 1 to 30 carbon atoms; at least two of R1 to R4 may be bonded together by an alkylidene radical containing an aryl or alkyl radical having 1 to 20 carbon atoms to form a ring;

R6 to R6''' are each independently a hydrogen atom; a halogen radical; an alkyl radical having 1 to 20 carbon atoms; or an aryl radical having 6 to 20 carbon atoms; and at least two of R6 to R6''' may be bonded together to form a fused ring;

A is a nitrogen or phosphorous atom;

CY1 is an aliphatic ring having 5 to 20 carbon atoms;

Q1 and Q2 are each independently a halogen radical; an alkylamido radical having 1 to 20 carbon atoms; an arylamido radical having 6 to 20 carbon atoms; an alkyl radical having 1 to 20 carbon atoms; an alkenyl radical having 2 to 20 carbon atoms; an aryl radical having 6 to 20 carbon atoms; an alkylaryl radical having 7 to 20 carbon atoms; an arylalkyl radical having 7 to 20 carbon atoms; or an alkylidene radical having 1 to 20 carbon atoms; and M is a Group 4 transition metal;

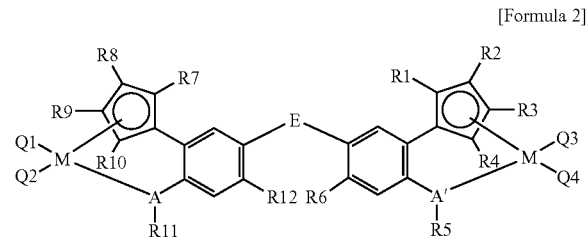

[Formula 2]

wherein

R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;

R5 and R11 is an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom;

E is a covalent bridging group for bridging two phenylene rings, which is an epoxy group; an epithio group; a carbonyl group; a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms;

Q1 to Q4 are each independently a halogen radical; an alkylamido radical having 1 to 20 carbon atoms; an arylamido radical; an alkyl radical having 1 to 20 carbon atoms; an alkenyl radical; an aryl radical; an alkylaryl radical; an arylalkyl radical; or an alkylidene radical having 1 to 20 carbon atoms; and M is a Group 4 transition metal;

—[Al(R31)-O]$_a$—      [Formula 3]

wherein R31's are each independently a halogen radical; a hydrocarbyl radical having 1 to 20 carbon atoms; or a halogen-substituted hydrocarbyl radical having 1 to 20 carbon atoms; and a is an integer of 2 or more; and J(R32)$_3$      [Formula 4]

wherein J is aluminum or boron; R32's are each independently a halogen radical; a hydrocarbyl radical having 1 to 20 carbon atoms; or a halogen-substituted hydrocarbyl radical having 1 to 20 carbon atoms; and

[L-H]$^+$[Z(R33)$_4$]$^-$ or [L]$^+$[Z(R33)$_4$]$^-$      [Formula 5]

wherein L is a neutral or cationic Lewis acid; H is a hydrogen atom; Z is a Group 13 element; R33's are each independently an alkyl or aryl radical having 6 to 20 carbon atoms, having at least one hydrogen atom substituted with halogen; a hydrocarbyl radical having 1 to 20 carbon atoms; or an alkoxy or phenoxy radical.

The present invention also provides a method for preparing the catalyst composition, comprising the steps of: a) contacting at least one transition metal compound selected from the group consisting of a transition metal compound of the formula 1 and a transition metal compound of the formula 2, with a compound represented by the formula 3 or 4 to obtain a mixture; and b) adding a compound represented by the formula 5 to the mixture obtained in the a) step.

The present invention also provides a method for preparing the catalyst composition, comprising a step of contacting at least one transition metal compound selected from the group consisting of a transition metal compound of the formula 1 and a transition metal compound of the formula 2, with a compound represented by the formula 3 to obtain a mixture.

The present invention also provides a method for preparing the catalyst composition, comprising a step of contacting at least one transition metal compound selected from the group consisting of a transition metal compound of the formula 1 and a transition metal compound of the formula 2, with a compound represented by the formula 5 to obtain a mixture.

The present invention also provides a method for preparing a polyolefin having a double composition distribution, comprising a step of contacting the catalyst composition and an olefin monomer.

Advantageous Effects

According to the present invention, the catalyst composition comprising a novel structure of a Group 4 transition metal compound can be used to prepare a polyolefin having a high molecular weight, high copolymerizability, or the like with a high activity even at a high polymerization temperature and a polyolefin copolymer having a double composition distribution.

BEST MODE FOR CARRYING OUT THE INVENTION

Hereinbelow, the present invention will be described in detail.

The transition metal compound used for the catalyst composition according to the present invention is characterized in that it represented by the formula 1 or 2. The transition metal compound of the formula 1 used for the catalyst composition according to the present invention has an amido or phosphorous ligand linked via a phenylene bridge, unlike the conventional transition metal compounds that have ligands comprising cyclopentadiene. Further, the transition metal compound of the formula 2 is configured such that a cyclopentadienyl group and an amido or phosphorous group are bridged via a phenylene bridge, and two single metal compounds formed by the binding of the metal positions are linked by a bridging group located on the phenylene bridge. From this, the transition metal compound of the formula 1 or 2 can stably maintain a rigid pentagon ring structure which allows easier approach to a monomer having large structurally steric hindrance. Further, the catalyst composition comprising the transition metal compound exhibits high activity and high comonomer reactivity, and allows the preparation of a polyolefin polymer having a double composition distribution. Further, the transition metal compounds can be prepared in a simple manner with high yield, by using a suzuki-coupling reaction for linking the cyclopentadienyl group and the phenylene bridge, and thus the transition metal compounds can have the structure that provide various electronic or steric environment surrounding the metal.

Specifically, in the mononuclear transition metal compound of the formula 1, the cyclopentadienyl group (Cp), and the amido group or phosphorous group are linked via a phenylene bridge, and thus there is tendency that structurally the Cp-M-A angle keeps narrow, while the Q1-M-Q2 angle for approach of the monomers keeps wide. Further, to be contrary with the CGC structure having a linkage via a silicon bridge, for example, the compound structure represented by the formula 1 has a stable and rigid pentagon ring structure having metal positions with a cyclopentadienyl ring (Cp), a phenylene bridge, and a nitrogen or phosphorous atom. In the binuclear transition metal compound represented by the formula 2, two single metal compounds are linked by a bridging group located on the phenylene bridge, and the metal compounds are configured that the cyclopentadienyl derivative (Cp) and the amido group or phosphorous group are linked by the phenylene bridge. Thus, it is characterized in that structurally the Cp-M-A angle keeps narrow, while the Q1-M-Q2 and Q3-M-Q4 angles for approach of the monomers keeps wide. To be contrary with the CGC structure having a linkage via a silicon bridge, for example, in the compound structure represented by the formula 2, a Cp, a phenylene bridge, and a nitrogen or phosphorous atom constitute a stable and rigid pentagon ring structure with the metal positions, and the reactivities of the two metal positions are highly likely to affect with each other. Therefore, it is expected that it is possible that if these compounds are reacted with a cocatalyst such as methylaluminoxane and $B(C_6F_5)_3$ for activation, and then used in the olefin polymerization, a polyolefin having the characteristics such as high activity, high molecular weight, and high copolymerizability is produced. In particular, in the structural characteristics of the catalyst, an ultra-low-density polyolefin copolymer having a density less than 0.910 g/cc can be prepared due to potential introduction of a large amount of alpha-olefins, as well as a linear low-density polyethylene having a density of about 0.910 to 0.930 g/cc. Further, various substituents can be introduced to a the cyclopentadienyl ring, the nitrogen or phosphorous atom, and the phenylene ring, wherein the electronic or steric environment can be easily regulated according to the kinds of the introduced substituents, and thus the structure and the physical properties of the resulting polyolefin can be controlled.

In particular, if the transition metal compound having the structure of the formula 1 is used for olefin polymerization, a polymer having a double composition distribution can be prepared. Specifically, the structure of the aliphatic ring represented by CY1 in the formula 1 is cyclopentyl, cyclohexyl, cycloheptyl, cyclooctyl, or the like, but not limited thereto, and it can be any aliphatic ring having 5 to 20 carbon atoms.

Of course, if the transition metal compound having a structure of the formula 2 is also used for olefin polymerization, a polymer having double composition distribution can be prepared.

In the present invention, R1 and R4; R2 and R3; and R6 to R6''' are preferably the same to each other in the formula 1.

In the present invention, the compound of the formula 1 is preferably a compound of the following formula 6.

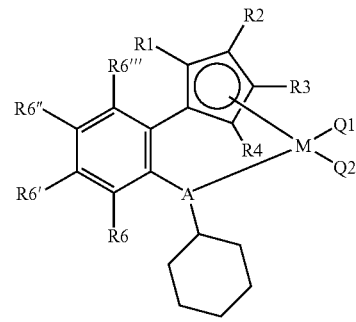

[Formula 6]

wherein R1 to R4, R6 to R6''', A, Q1, Q2 and M each have the same meanings as defined in the formula 1.

In the present invention, R1, R4, R7 and R10; R2, R3, R8 and R9; R6 and R12; and R5 and R11 are preferably the same to each other in the formula 2.

In the present invention, a compound represented by the following formula 7 is preferred as a compound which is desirable for easy regulation of the electronic or steric effects around the metal in the formula 2.

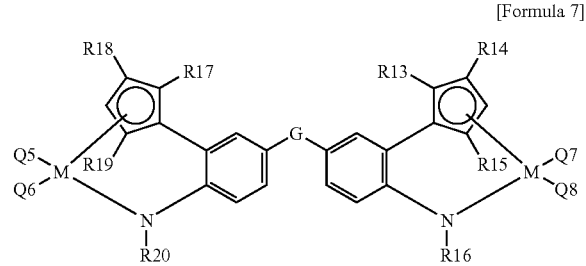

[Formula 7]

wherein

R13 to R15, and R17 to R19 are each independently a hydrogen atom; or an alkyl radical having 1 to 20 carbon atoms; an aryl radical; or a silyl radical;

R16 and R20 are each independently an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; or an arylalkyl radical;

Q5 to Q8 are each independently a halogen radical; an alkylamido radical having 1 to 20 carbon atoms; an arylamido radical; or an alkyl radical having 1 to 20 carbon atoms;

G is an epoxy group; an epithio group; a carbonyl group; a heterohydrocarbylene group having 1 to 60 carbon atoms, substituted with a substituent containing an oxygen or nitrogen atom; or —C(R21)$_2$— (wherein R21 is hydrogen, or alkyl having 1 to 20 carbon atoms; aryl; silyl; alkenyl having 2 to 20 carbon atoms; alkylaryl; or arylalkyl); or a metalloid radical of a Group 14 metal substituted with hydrocarbyl; and M is a Group 4 transition metal.

As G, the hydrocarbylene group having 1 to 60 carbon atoms is more preferably a hydrocarbylene group having 10 or less carbon atoms such as methylidene, ethylidene, propylidene, butylidene, and pentylidene.

The compound of the formula 7 is preferably a compound represented by the following formula 8.

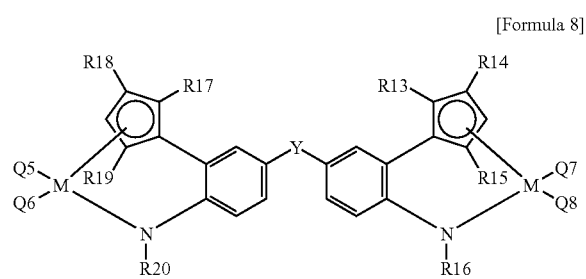
[Formula 8]

wherein
Y is —CH$_2$—, —C(CH$_3$)$_2$—, —C(=O)—, —C(=NR22)-, —O— or —S— (wherein R22 is a hydrogen atom; an alkyl radical having 1 to 20 carbon atoms; an aryl radical; a silyl radical; an alkenyl radical having 2 to 20 carbon atoms; an alkylaryl radical; or an arylalkyl radical;

R13 to R20, Q5 to Q8, and M each have the same meanings as defined in the formula 7.

The compound of the formula 2 is preferably a compound represented by the following formula 9.

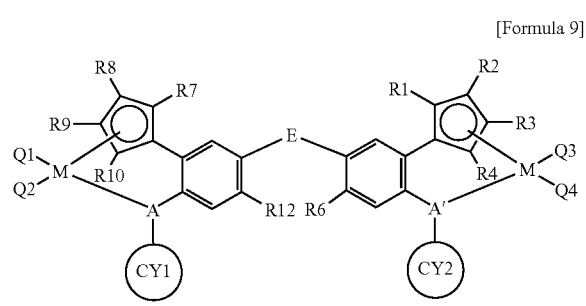
[Formula 9]

wherein
R1 to R4, R6 to R10, R12, Q1 to Q4, A, A', E and M each have the same meanings as defined in the formula 2, and CY1 and CY2 are each independently an aliphatic ring having 5 to 20 carbon atoms.

The compound of the formula 9 is preferably a compound represented by the following formula 10.

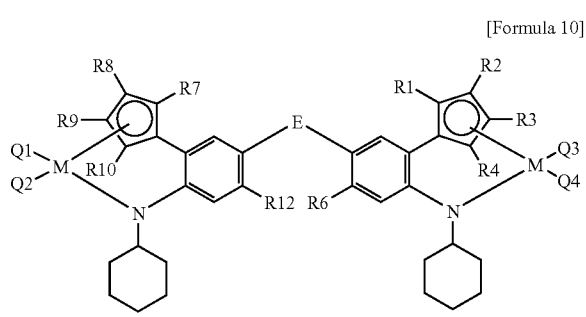
[Formula 10]

wherein R1 to R4, R6 to R10, R12, Q1 to Q4, E and M each have the same meanings as defined in the formula 9.

In the present invention, the binuclear transition metal compound of the formula 2 is particularly preferably represented by one of the following structures:

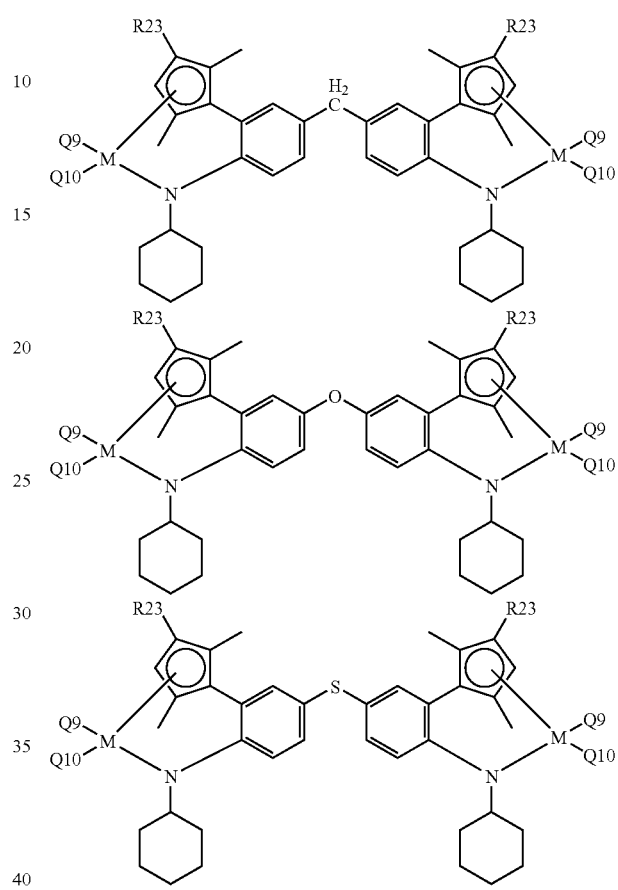

In the above structures,

R23 is selected from hydrogen and a methyl radical, and Q9 and Q10 are each independently selected from methyl, dimethylamido, diethylamido and chloride radicals.

In the present specification, each of the substituents will be described in detail.

The alkyl radical having 1 to 20 carbon atoms may be linear or branched, and examples thereof include a methyl group, an ethyl group, a propyl group, an isopropyl group, a butyl group, a tert-butyl group, a pentyl group, a hexyl group, and a heptyl group, but are not limited thereto.

The aryl radical preferably contains 6 to 20 carbon atoms, and specifically examples thereof include a phenyl group, a naphthyl group, an anthracenyl group, a biphenyl group, a pyrenyl group and a perylenyl group, but are not limited thereto.

Examples of the silyl radical include trimethylsilyl, triethylsilyl, tri-iso-propylsilyl, tri-t-butylsilyl, and triphenylsilyl, but are not limited thereto.

The alkenyl radical may be linear or branched, and preferably contains 2 to 20 carbon atoms. Specifically, examples thereof include vinyl, 1-propenyl, 2-propenyl, isopropenyl, 1-butenyl, 2-butenyl, 3-butenyl, 1-pentenyl, 2-pentenyl, 3-pentenyl, 3-methyl-1-butenyl, 1,3-butadenyl, 1-octenyl, 1-decenyl, and 1-octadecenyl, but are not limited thereto.

The alkylaryl radical means aryl substituted with the above-described alkyl, and preferably contains 7 to 20 carbon atoms.

The arylalkyl radical means alkyl substituted with the above-described aryl, and preferably contains 7 to 20 carbon atoms.

Examples of the Group 4 transition metal include Ti, Zr and Hf.

The hydrocarbyl radical means a monovalent substituent formed by the removal of a hydrogen atom from hydrocarbon, preferably contains 1 to 60 carbon atoms, more preferably 1 to 30 carbon atoms. Specifically, examples thereof include alkyl, alkenyl, alkynyl, aryl, alkylaryl, and arylalkyl, but are not limited thereto.

The metalloid comprehensively refers to a metal having similar properties to both metals and non-metals. Examples thereof include boron, silicon, arsenide, antimony, and tellurium, but are not limited thereto.

In the present invention, the substituent of the substituted hydrocarbylene group or the substituted heterohydrocarbylene group is preferably halogen, alkyl having 1 to 20 carbon atoms, alkoxy having 1 to 20 carbon atoms, or aryl having 6 to 20 carbon atoms, but are not limited thereto. Any other substituent available in the art can be used for this.

In the catalyst composition according to the present invention, the compound represented by the formula 3 or 4 can be otherwise represented by an alkylating agent, and the compound represented by the formula 5 can be represented by an activating agent.

The catalyst composition exists in the state activated by the reaction of the transition metal compound with the cocatalysts, which may be referred to as an activated catalyst composition. However, since it is well known in the art that the catalyst composition exists in the activated state, it would not to particularly use the term "activated catalyst composition" in the present specification. The catalyst composition can be used for olefin homopolymerization or copolymerization.

Firstly, the present invention provides a method for preparing the catalyst composition, comprising the steps of: a) contacting at least one transition metal compound selected from the group consisting of a transition metal compound of the formula 1 and a transition metal compound of the formula 2, with a compound represented by the formula 3 or 4 to obtain a mixture; and b) adding a compound represented by the formula 5 to the mixture obtained in the a) step.

Secondly, the present invention provides a method for preparing the catalyst composition, comprising a step of contacting at least one transition metal compound selected from the group consisting of a transition metal compound of the formula 1 and a transition metal compound of the formula 2, with a compound represented by the formula 3 to obtain a mixture.

Third, the present invention provides a method for preparing the catalyst composition, comprising a step of contacting at least one transition metal compound selected from the group consisting of a transition metal compound of the formula 1 and a transition metal compound of the formula 2, with a compound represented by the formula 5 to obtain a mixture.

In the first method of the methods for preparing the catalyst composition, the molar ratio of the compound represented by the formula 3 or 4 to the transition metal compound of the formula 1 or 2 is preferably 1:2 to 1:5,000, more preferably 1:10 to 1:1,000, and most preferably 1:20 to 1:500.

Moreover, the molar ratio of the compound represented by the formula 5 to the transition metal compound of the formula 1 or 2 is preferably 1:1 to 1:25, more preferably 1:1 to 1:10, and most preferably 1:2 to 1:5.

In the first method for preparing the catalyst composition, if the molar ratio of the compound represented by the formula 3 or 4 to the transition metal compound of the formula 1 or 2 is less than 1:2, the amount of the alkylating agent is too low, which causes a problem of not completely performing alkylation of the metal compound. If the molar ratio is more than 1:5,000, the metal compound is alkylated but the side reaction between the remaining excessive amount of the alkylating agent and the activating agent of the formula 5 causes a problem of not completely performing activation of the alkylated metal compound. Moreover, if the molar ratio of the compound represented by the formula 5 to the transition metal compound of the formula 1 or 2 is less than 1:1, the amount of the activating agent is relatively low, which causes a problem of not completely performing activation of the transition metal compound, and thus of lowering the activity of the resulting catalyst composition. If the molar ratio is more than 1:25, there is a problem that the metal compound is completely activated, but the remaining excessive amount of the activating agent increases the cost of the catalyst composition or the purity of the resulting polymer is lowered.

In the second method for preparing the catalyst composition, if the molar ratio of the compound represented by the formula 3 to the transition metal compound of the formula 1 or 2 is preferably 1:10 to 1:10,000, more preferably 1:100 to 1:5,000, and most preferably 1:500 to 1:2000.

If the molar ratio is less than 1:10, the amount of the activating agent is relatively low, which causes a problem of not completely performing activation of the metal compound, and thus of lowering the activity of the resulting catalyst composition. If the molar ratio is more than 1:10,000, there is a problem that the metal compound is completely activated, but the remaining excessive amount of the activating agent increases the cost of the catalyst composition or the purity of the resulting polymer is lowered.

Moreover, in the third method for preparing the catalyst composition, if the molar ratio of the compound represented by the formula 5 to the transition metal compound of the formula 1 or 2 is preferably 1:1 to 1:25, more preferably 1:1 to 1:10, and most preferably 1:2 to 1:5.

If the molar ratio of the compound represented by the formula 5 to the transition metal compound of the formula 1 or 2 is less than 1:1, the amount of the activating agent is relatively low, which causes a problem of not completely performing activation of the metal compound, and thus of lowering the activity of the resulting catalyst composition. If the molar ratio is more than 1:25, there is a problem that the metal compound is completely activated, but the remaining excessive amount of the activating agent increases the cost of the catalyst composition or the purity of the resulting polymer is lowered.

In the preparation of the catalyst composition, as the reaction solvent, a hydrocarbon solvent such as pentane, hexane and heptane, or an aromatic solvent such as benzene and toluene can be used, but not limited thereto. All of the solvents available in the art can be used.

The transition metal compounds of the formula 1 or 2 and the cocatalysts can be used as supported on silica or alumina.

The compound represented by the formula 3 is not particularly limited as long as it is alkylaluminoxane, and preferable examples thereof include methylaluminoxane, ethylaluminoxane, isobutylaluminoxane and butylaluminoxane, among which methylaluminoxane is a particularly preferred compound.

The alkyl metal compound represented by the formula 4 is not particularly limited, and preferable examples thereof include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethyllaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, and tributylboron, among which a particularly preferred compound is selected from trimethylaluminum, triethylaluminum, and triisobutylaluminum.

Examples of the compound represented by the formula 5 include triethylammoniumtetra(phenyl)boron, tributylammoniumtetra(phenyl)boron, trimethylammoniumtetra(phenyl)boron, tripropylammoniumtetra(phenyl)boron, trimethylammoniumtetra(p-tolyl)boron, trimethylammoniumtetra(o, p-dimethylphenyl)boron, tributylammoniumtetra(p-trifluoromethylphenyl)boron, trimethylammoniumtetra(p-trifluoromethylphenyl)boron, tributylammoniumtetra(pentafluorophenyl)boron, N,N-diethylaniliniumtetra(phenyl)boron, N,N-diethylaniliniumtetra(phenyl)boron, N,N-diethylaniliniumtetra(pentafluorophenyl)boron, diethylammoniumtetra(pentafluorophenyl)boron, triphenylphosphoniumtetra(phenyl)boron, trimethylphosphoniumtetra(phenyl)boron, tripropylammoniumtetra(p-tolyl)boron, triethylammoniumtetra(o,p-dimethylphenyl)boron, N,N-diethylaniliniumtetra(phenyl)boron, triphenylcarboniumtetra(p-trifluoromethylphenyl)boron, triphenylcarboniumtetra(pentafluorophenyl)boron, trityltetra(pentafluorophenyl)boron, triethylammoniumtetra(phenyl)aluminum, tributylammoniumtetra(phenyl)aluminum, trimethylammoniumtetra(phenyl)aluminum, tripropylammoniumtetra(phenyl)aluminum, trimethylammoniumtetra(p-tolyl)aluminum, tripropylammoniumtetra(p-tolyl)aluminum, triethylammoniumtetra(o, p-dimethylphenyl)aluminum, tributylammoniumtetra(p-trifluoromethylphenyl)aluminum, trimethylammoniumtetra(p-trifluoromethylphenyl)aluminum, tributylammoniumtetra(pentafluorophenyl)aluminum, N,N-diethylaniliniumtetra(phenyl)aluminum, N,N-diethylaniliniumtetra(phenyl)aluminum, N,N-diethylaniliniumtetra(pentafluorophenyl)aluminum, diethylammoniumtetra(pentafluorophenyl)aluminum, triphenylphosphoniumtetra(phenyl)aluminum, trimethylphosphoniumtetra(phenyl)aluminum, triethylammoniumtetra(phenyl)aluminum, tributylammoniumtetra(phenyl)aluminum, etc.

Further, the present invention provides a method for preparing a polyolefin having a double composition distribution, using the catalyst composition. Specifically, the present invention provides a method for preparing a polyolefin having a double composition distribution, comprising a step of contacting the catalyst composition and at least one olefin monomer.

By using the activated catalyst composition, a copolymer having a high molecular weight, an ultralow density of 0.910 g/cc or less as a molecular density, and a double composition distribution as measured by a bimodal curve in DSC measurement can be prepared upon copolymerization reaction of ethyleme and a monomer having high steric hindrance such as 1-octene, even at a high reaction temperature of 90° C. or higher.

In the method for preparing a polyolefin according to the present invention, as the most preferable polymerization process using the catalyst composition is a solution process. The catalyst composition can be employed in a slurry or gas phase process, in combination with an inorganic carrier such as silica.

In the method for preparing a polyolefin according to the present invention, the catalyst composition can be dissolved or diluted with an aliphatic hydrocarbon solvent having 5 to 12 carbon atoms suitable for an olefin polymerization process, such as pentane, hexane, heptane, nonane, decane, and isomers thereof; an aromatic hydrocarbon solvent such as toluene and benzene; a hydrocarbon solvent substituted with chlorine such as dichloromethane and chlorobenzene, prior to injection. The solvent used herein is preferably used after removing a small amount of water, air, etc. which functions as a catalyst toxin, by treatment with a small amount of alkylaluminum, and a cocatalyst can be additionally used therefor.

Examples of the olefin monomers which are polymerizable with the transition metal compounds and the cocatalysts include ethylene, alpha-olefins, cyclic olefins, etc. Additionally, examples of the olefin monomers include diene olefin monomers and triene olefin monomers having two or more double bonds. Specific examples of the monomers include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbornadiene, ethylidenenorbornene, phenyl-norbornene, vinylnorbornene, dicyclopentadiene, 1,4-butadiene, 1,5-pentadiene, 1,6-hexadiene, styrene, alpha-methylstyrene, divinylbenzene, 3-chloromethylstyrene, etc. and two or more kinds of the monomers can be mixed for copolymerization. In the present invention, among the above monomers, preferred is at least one monomer selected from ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene and 1-eicosene.

The polyolefin prepared according to the method of the present invention may be either of a homopolymer and a copolymer. If the polyolefin is a copolymer made from ethylene and the monomer other than ethylene, the monomers constituting the copolymer is preferably ethylene, and at least one monomer selected from propylene, 1-butene, 1-hexene, 4-methyl-1-pentene, and 1-octene.

Mode for the Invention

Hereinafter, the present invention will be described in more detail by means of Examples, but the scope of the invention is not limited thereto.

EXAMPLE

The organic reagent and the solvent were purchased from Aldrich Chemical Company and Merck limited, and purified using a standard method for use. In all the steps for synthesis, contact with air and the moisture was avoided to increase the reproductivity of the experiments. In order to demonstrate the structure of the compound, 400 MHz Nuclear Magnetic Resonance Spectrometer (NMR) and X-ray Spectrometer were used for each spectrum and diagrams.

The melt index (MI) of the resulting polymer was measured in accordance with ASTM D-1238 (Condition E, 190° C., a load of 2.16 Kg). The melting point (Tm) of the polymer was determined using a DSC (Differential Scanning Calorimeter) 2920 manufactured by TA Instruments. That is, the temperature was raised to 200° C., maintained at that temperature for 5 minutes, lowered to 30° C., and then raised, and thereafter the peak of the DSC curve was taken as a melting point. At that time, the temperature raising and lowering rates are 10° C./min and the melting point is obtained during the second temperature elevation.

Further, the density of the polymer was measured by using a sample treated with an antioxidant (1,000 ppm) to prepare a sheet having a thickness of 3 mm and a radius of 2 cm using a press mold at 180° C., and cooling the sheet at 10° C./min, and measuring the density with a Mettler scale.

Synthesis of Ligand Transition Metal Compound

Example 1

2-Dihydroxyboryl-3,4-dimethyl-2-cyclopenten-1-one

To a 1000-mL flask, 2-bromo-3,4-dimethyl-2-cyclopenten-1-one ethylene ketal (57.3 g, 246 mmol) and THF (300 mL) were added and mixed. The flask temperature was lowered to −78° C., and n-BuLi (2.5M in Hexane, 98.3 mL, 245 mmol) was charged thereinto. The temperature was maintained at −78° C., and after 1 hour, boron triisopropyl ester (50.9 g, 270 mmol) was added, and the mixture was stirred for 1.5 hours. Then, the temperature was raised, and at −30° C., it was further stirred for 30 minutes, and then to the flask, 2 N HCl (300 mL) was immediately added. The solution added with the aqueous solution was transferred to a separatory funnel, and an organic layer was extracted from ethanol (300 mL). Then, the organic layer was further extracted from ethanol (300 mL) twice. Water was removed from the combined organic layer over $MgSO_4$, and filtered with a glass filter. The rotary evaporator was used to remove the solvent, thereby obtaining a solid. The obtained solid was pulverized in hexane, and then filtered to obtain 20.3 g of a final product.

$^1$H NMR (CDCl$_3$): δ 1.24 (d, J=3.6 Hz, 3H, CH$_3$), 2.09 (dd, J=19, 2.0 Hz, 1H, CH$_2$), 2.39 (s, 3H, CH$_3$), 2.72 (dd, J=19, 6.8 Hz, 1H, CH$_2$), 2.84-2.86 (m, 1H, CH), 7.29 (s, 2H, OH) ppm. $^{13}$C {$^1$H} NMR (CDCl$_3$): δ 18.01, 18.90, 40.76, 44.22, 197.08, 216.12 ppm. Anal. Calc. (C$_7$H$_{11}$BO$_3$): C: 54.60; H, 7.20%. Found: C, 54.40; H, 7.42

Example 2

2-Bromo-N-cyclohexylaniline

Into a 100-mL flask, 2-bromoaniline (1.65 g, 9.56 mmol), cyclohexanone (4.693 g, 47.81 mmol), benzene (9 ml) and molecular sieves (4 Å, 2.0 g) were put. To the flask, a Dean-Stark apparatus was connected for refluxing for 4 days. Then, the solution in the flask was cooled to normal temperature, and then filtered to remove the molecular sieves. The rotary evaporator was used to remove the solvent, and dried in vacuo at 60° C. to obtain an imine compound. The obtained imine compound was dissolved in degassed methanol (28 ml), sodium borohydride (1.08 g, 28.7 mmol) was slowly added under a nitrogen atmosphere, and then the mixture was stirred at normal temperature for 2 hours. Then, to the stirred solution, a 1 N aqueous KOH (20 mL) solution was added. The solution added with the aqueous solution was transferred to a separatory funnel and extracted from methylene chloride (30 mL) twice. Water was removed from the combined organic layer over MgSO$_4$, and filtered with a glass filter. The rotary evaporator was used to remove the solvent, thereby obtaining a residue. The obtained residue was separated by column chromatography to obtain colorless oil (1.43 g, 59%).

$^1$H NMR (CDCl$_3$): δ 0.99 (t, J=Hz, 2H, Cy), 1.29-1.53 (m, 3H, Cy), 1.72-1.75 (m, 1H, Cy), 1.88-1.84 (m, 2H, Cy), 2.11-2.14 (m, 2H, Cy), 3.36-3.40 (m, 1H, N—CH), 4.34 (br s, 1H, NH), 6.58 (td, J=7.6, 0.8 Hz, 1H, C$_6$H$_4$), 6.71 (d, J=7.6 Hz, 1H, C$_6$H$_4$), 7.20 (td, J=7.6, 0.8 Hz, 1H, C$_6$H$_4$), 7.47 (dd, J=7.6, 1.2 Hz, 1H, C$_6$H$_4$) ppm. $^{13}$C {$^1$H} NMR (CDCl$_3$): δ 24.91, 25.94, 33.13, 51.53, 109.62, 111.58, 116.92, 128.16, 132.33, 143.83 ppm. Anal. Calc. (C$_{12}$H$_{16}$BrN): C, 56.71; H, 6.35; N, 5.51%. Found: C, 56.67; H, 6.58; N, 5.82%

Example 3

N-cyclohexyl-4-methylaniline

Into a 100-mL flask, p-toluidine (3.85 g, 35.9 mmol), cyclohexanone (21.2 g, 0.216 mol), toluene (25 ml) and molecular sieves (4 Å, 7.0 g) were put. The flask was sealed, and the mixture was stirred at 100° C. for 2 days. Then, the molecular sieves were removed, and the resultant was dried in vacuo at 60° C. to obtain an imine compound. The obtained imine compound was dissolved in degassed methanol (28 ml), sodium borohydride (4.08 g, 108 mmol) was slowly added under a nitrogen atmosphere, and then the mixture was stirred at normal temperature for 2 hours. Then, to the stirred solution, a 1 N aqueous KOH (20 mL) solution was added. The solution added with the aqueous solution was transferred to a separatory funnel and extracted from methylene chloride (30 mL) twice. Water was removed from the combined organic layer over MgSO$_4$, and filtered with a glass filter. The rotary evaporator was used to remove the solvent, thereby obtaining a residue. The obtained residue was separated by column chromatography to obtain colorless oil (5.16 g, 76%).

$^1$H NMR (C$_6$D$_6$): δ 0.88-0.94 (m, 2H, Cy), 1.04-1.09 (m, 1H, Cy), 1.12-1.21 (m, 2H, Cy), 1.46-1.50 (m, 1H, Cy), 1.55-1.60 (m, 2H, Cy), 1.90-1.93 (m, 2H, Cy), 2.23 (s, 3H, CH$_3$), 3.03 (br s, 1H, NH), 3.04-3.10 (m, 1H, N—CH), 6.45 (d, J=8.0 Hz, 2H, C$_6$H$_4$), 7.00 (d, J=8.0 Hz, 2H, C$_6$H$_4$) ppm. $^{13}$C {$^1$H} NMR (C$_6$D$_6$): δ 20.85, 25.50, 26.50, 33.82, 52.04, 113.82, 125.78, 130.03, 145.60 ppm.

Example 4

2-Bromo-N-cyclohexyl-4-methylaniline

In a 100-mL flask, N-cyclohexyl-4-methylaniline (2.00 g, 10.6 mmol) was dissolved in methylene chloride (20 mL) and a solution of bromine (Br$_2$) (1.69 g, 10.6 mmol) dissolved in methylene chloride (16 ml) was injected at 0° C. for 30 minutes. Then, the solution was further stirred for 2 hours, and a 1 N aqueous KOH (20 mL) solution was added. The solution added with the aqueous solution was transferred to a separatory funnel and extracted from methylene chloride (40 mL) twice. Water was removed from the combined organic layer over MgSO$_4$, and filtered with a glass filter. The rotary evaporator was used to remove the solvent, thereby obtaining a residue. The obtained residue was separated by column chromatography to obtain colorless oil (2.67 g, 94%).

$^1$H NMR (C$_6$D$_6$): δ 0.98-1.03 (m, 3H, Cy), 1.10-1.16 (m, 3H, Cy), 1.39-1.42 (m, 1H, Cy), 1.53-1.56 (m, 2H, Cy), 1.82-1.85 (m, 2H, Cy), 2.03 (s, 3H, CH$_3$), 3.06-3.08 (m, 1H, N—CH), 4.16 (br d, J=7.2 Hz, 1H, NH), 6.46 (d, J=7.6 Hz, 1H, C$_6$H$_3$), 6.84 (dd, J=1.6, 7.6 Hz, 1H, C$_6$H$_3$), 7.23 (d, J=1.6

Hz, 1H, C$_6$H$_3$) ppm. $^{13}$C {$^1$H} NMR (C$_6$D$_6$): δ 20.25, 25.21, 26.29, 33.37, 51.90, 110.25, 112.29, 126.71, 129.24, 133.29, 142.34 ppm.

Example 5

N-Cyclohexyl-4-phenylaniline

The same procedure was carried out in the same manner as in Example 3 except that benzidine was used instead of p-toluidine to obtain a yellow solid compound (65%).

$^1$H NMR (C$_6$D$_6$): δ 0.84-0.94 (m, 2H, Cy), 1.02-1.21 (m, 3H, Cy), 1.46-1.59 (m, 3H, Cy), 1.88-1.91 (m, 2H, Cy), 3.06-3.11 (m, 1H, N—CH), 3.18 (br s, 1H, NH), 6.49 (d, J=8.0 Hz, 2H, C$_6$H$_4$), 7.14 (t, J=8.0 Hz, 1H, C$_6$H$_5$), 7.28 (t, J=8.0 Hz, 2H, C$_6$H$_5$), 7.49 (d, J=8.0 Hz, 2H, C$_6$H$_4$), 7.60 (d, J=8.0 Hz, 2H, C$_6$H$_5$) ppm. $^{13}$C {$^1$H} NMR (C$_6$D$_6$): δ 25.43, 26.41, 33.66, 51.70, 113.78, 126.15, 126.59, 128.27, 129.00, 130.10, 142.03, 147.14 ppm.

Example 6

2-Bromo-N-cyclohexyl-4-phenylaniline

The same procedure was carried out in the same manner as in Example 4 except that N-cyclohexyl-4-phenylaniline was used instead of N-cyclohexyl-4-methylaniline to obtain a colorless oil compound (73%).

$^1$H NMR (C$_6$D$_6$): δ 0.96-1.05 (m, 2H, Cy), 1.06-1.18 (m, 2H, Cy), 1.23-1.31 (m, 1H, Cy), 1.39-1.44 (m, 1H, Cy), 1.52-1.56 (m, 2H, Cy), 1.79-1.83 (m, 2H, Cy), 3.02-3.11 (m, 1H, N—CH), 4.35 (br d, J=7.2 Hz, 1H, NH), 6.52 (d, J=8.0 Hz, 1H, C$_6$H$_3$), 7.11 (tt, J=1.6, 8.0 Hz, 1H, C$_6$H$_5$), 7.21 (t, J=8.0 Hz, 2H, C$_6$H$_5$), 7.34 (dd, J=2.4, 8.4 Hz, 1H, C$_6$H$_5$), 7.37 (dd, J=1.2, 8.0 Hz, 2H, C$_6$H$_5$), 7.78 (d, J=2.4 Hz, 1H, C$_6$H$_3$) ppm. $^{13}$C {$^1$H} NMR (C$_6$D$_6$): δ 25.13, 26.20, 33.22, 51.70, 110.72, 112.28, 126.56, 126.62, 127.36, 129.02, 130.93, 131.42, 140.42, 143.67 ppm.

Example 7

4-Chloro-N-cyclohexylaniline

The same procedure was carried out in the same manner as in Example 3 except that 4-chloroaniline was used instead of p-toluidine to obtain a white solid compound (71%).

$^1$H NMR (C$_6$D$_6$): δ 0.77-0.85 (m, 2H, Cy), 1.01-1.17 (m, 3H, Cy), 1.45-1.56 (m, 3H, Cy), 1.76-1.79 (m, 2H, Cy), 2.85-2.90 (m, 1H, N—CH), 3.03 (br s, 1H, NH), 6.15 (d, J=8.8 Hz, 2H, C$_6$H$_4$), 7.09 (d, J=8.8 Hz, 2H, C$_6$H$_4$) ppm. $^{13}$C {$^1$H} NMR (C$_6$D$_6$): δ 25.36, 26.34, 33.44, 51.70, 114.42, 121.31, 129.30, 146.21 ppm

Example 8

2-Bromo-4-chloro-N-cyclohexylaniline

The same procedure was carried out in the same manner as in Example 4 except that 4-chloro-N-cyclohexylaniline was used instead of N-cyclohexyl-4-methylaniline to obtain a colorless oil compound (90%).

$^1$H NMR (C$_6$D$_6$): δ 0.82-0.93 (m, 2H, Cy), 0.96-0.98 (m, 1H, Cy), 1.00-1.11 (m, 2H, Cy), 1.37-1.41 (m, 1H, Cy), 1.36-1.41 (m, 2H, Cy), 1.66-1.69 (m, 2H, Cy), 2.79-2.90 (m, 1H, N—CH), 4.14 (br d, J=7.2 Hz, 1H, NH), 6.16 (d, J=8.8 Hz, 1H, C$_6$H$_3$), 6.98 (dd, J=2.8, 8.8 Hz, 1H, C$_6$H$_3$), 7.38 (d, J=2.8 Hz, 1H, C$_6$H$_3$) ppm. $^{13}$C {$^1$H} NMR (C$_6$D$_6$): δ 25.06, 26.15, 33.03, 51.68, 109.87, 112.42, 121.04, 128.57, 132.16, 143.12 ppm

Example 9

N-Cyclohexyl-4-fluoroaniline

The same procedure was carried out in the same manner as in Example 3 except that 4-fluoroaniline was used instead of p-toluidine to obtain a brown oil compound (92%).

$^1$H NMR (C$_6$D$_6$): δ 0.83-0.92 (m, 2H, Cy), 1.00-1.22 (m, 3H, Cy), 1.47-1.52 (m, 1H, Cy), 1.56-1.60 (m, 2H, Cy), 1.82-1.85 (m, 2H, Cy), 2.89-2.95 (m, 1H, N—CH), 3.00 (br s, 1H, NH), 6.22 (dd, J=4.4, 8.8 Hz, 2H, C$_6$H$_4$), 6.79 (t, J=8.8 Hz, 2H, C$_6$H$_4$) ppm. $^{13}$C {$^1$H} NMR (C$_6$D$_6$): δ 25.45, 26.43, 33.64, 52.33, 114.13 (d, $^3J_{CF}$=6.8 Hz, C$_6$H$_4$F), 155.78 (d, $^2J_{CF}$=22 Hz, C$_6$H$_4$F), 144.18 (d, $^4J_{CF}$=1.5 Hz, C$_6$H$_4$F—C), 155-66 (d, $^1J_{CF}$=231.3 Hz, C$_6$H$_4$F—C) ppm

Example 10

2-Bromo-N-cyclohexyl-4-fluoroaniline

The same procedure was carried out in the same manner as in Example 4 except that N-cyclohexyl-4-fluoroaniline was used instead of N-cyclohexyl-4-methylaniline to obtain a colorless oil compound (90%).

$^1$H NMR (C$_6$D$_6$): δ 0.90-0.99 (m, 2H, Cy), 1.03-1.19 (m, 3H, Cy), 1.42-1.46 (m, 1H, Cy), 1.53-1.57 (m, 2H, Cy), 1.75-1.78 (m, 2H, Cy), 2.87-2.96 (m, 1H, N—CH), 3.97 (d, J=7.2 Hz, 1H, NH), 6.23 (dd, J=4.4, 8.8 Hz, 1H, C$_6$H$_3$), 6.72 (td, J=2.8, 8.8 Hz, 1H, C$_6$H$_3$), 7.09 (dd, J=2.8, 8.0 Hz, 1H, C$_6$H$_3$) ppm. $^{13}$C {$^1$H} NMR (C$_6$D$_6$): δ 25.20, 26.28, 33.29, 52.15, 109.14 (d, $^3J_{CF}$=9.9 Hz, C$_6$H$_3$), 111.99 (d, $^3J_{CF}$=7.6 Hz, C$_6$H$_3$), 115.21 (d, $^2J_{CF}$=21.2 Hz, C$_6$H$_3$), 119.71 (d, $^3J_{CF}$=25 Hz, C$_6$H$_3$), 141.26 (d, $^4J_{CF}$=2.3 Hz, C$_6$H$_3$), 154.32 (d, J$_{CF}$=236 Hz, C$_6$H$_3$) ppm

Example 11

2-(2-Aminophenyl)-3,4-dimethyl-2-cyclopenten-1-one

Into a 100-mL Schlenk flask, 2-dihydroxyboryl-3-methyl-2-cyclopenten-1-one (1.27 g, 8.26 mmol), tetrakis(triphenylphosphine)palladium (0.182 g, 0.157 mmol) and sodium carbonate (1.25 g, 11.8 mmol) were put, and then degassed DME (21 μL) and distilled water (7 mL) purged with nitrogen gas were put thereto using a syringe. Then, to the flask, 2-bromo-N-cyclohexylaniline (2.00 g, 7.87 mmol) was put using a syringe, and was subject to reaction at 95° C. for 12 hours.

Thereafter, the reaction solution was transferred to a separatory funnel, and ethyl acetate (200 mL) and H$_2$O (100 mL) were additionally added to the separatory funnel to extract an organic layer. The aqueous solution layer was further extracted from ethyl acetate (100 mL). Water was removed from the combined organic layer over MgSO$_4$, and filtered with a glass filter. The rotary evaporator was used to remove the remaining solvent, thereby obtaining a final product (1.23 g).

$^1$H NMR (CDCl$_3$): δ 1.13-1.28 (m, 4H, Cy), 1.32 (d, J=6.8 Hz, 3H, CH$_3$), 1.35-1.41 (m, 2H, Cy), 1.62-1.65 (m, 1H, Cy), 1.71-1.75 (m, 2H, Cy), 2.03 (s, 3H, CH$_3$), 1.98-2.07 (m, 1H, Cy), 2.19 (d, J=18.4 Hz, 1H, CH$_2$), 2.83 (dd, J=18.8, 6.8 Hz, 1H, CH$_2$), 2.95 (quintet, J=6.8 Hz, 1H, CH), 3.24-3.29 (m, 1H, N—CH), 3.48 (s, 1H, NH), 6.71 (t, J=8.8 Hz, 1H, C$_6$H$_4$), 6.74 (d, J=8.8 Hz, 1H, C$_6$H$_4$), 6.88 (d, J=8.8 Hz, 1H, C$_6$H$_4$), 7.20 (t, J=8.8 Hz, 1H, C$_6$H$_4$) ppm. $^{13}$C {$^1$H} NMR (CDCl$_3$): δ 16.31, 19.54, 24.82, 25.88, 33.13, 37.59, 43.52, 51.43, 111.34, 116.13, 117.19, 128.89, 129.44, 130.39, 144.72, 178.62, 206.65 ppm

Example 12

2-(2-Cyclohexylamino-4-methylphenyl)-3,4-dimethyl-2-cyclopenten-1-one

The same procedure was carried out in the same manner as in Example 11 except that 2-bromo-N-cyclohexyl-4-methylaniline was used instead of 2-bromo-N-cyclohexylaniline to obtain a yellow oil compound (98%).

$^1$H NMR (C$_6$D$_6$): δ 0.77 (d, J=6.8 Hz, 3H, CH$_3$), 1.10-1.22 (m, 4H, Cy), 1.42-1.48 (m, 2H, Cy), 1.54-1.62 (m, 2H, Cy), 1.63 (s, 3H, CH$_3$), 1.86 (dd, J=2.4, 18.4 Hz, 1H, CH$_2$), 1.96-2.06 (m, 2H, Cy), 2.18-2.23 (m, 1H, CH), 2.25 (s, 3H, C$_6$H$_3$—CH$_3$), 2.46 (dd, J=6.8, 18.4 Hz, 1H, CH$_2$), 3.14-3.24 (m, 1H, N—CH), 3.84 (br s, 1H, NH), 6.73 (d, J=8.4 Hz, 1H, C$_6$H$_3$), 6.86 (br s, 1H, C$_6$H$_3$), 7.08 (dd, J=2.4, 8.4 Hz, 1H, C$_6$H$_3$) ppm. $^{13}$C {$^1$H} NMR (C$_6$D$_6$): δ 16.19, 19.50, 20.81, 25.32, 26.53, 33.75, 37.67, 43.78, 52.02, 112.29, 119.07, 125.25, 129.85, 131.90, 139.93, 143.96, 176.77, 205.26 ppm

Example 13

2-(2-Cyclohexylamino-4-phenylphenyl)-3,4-dimethyl-2-cyclopenten-1-one

The same procedure was carried out in the same manner as in Example 11 except that 2-bromo-N-cyclohexyl-4-phenylaniline was used instead of 2-bromo-N-cyclohexylaniline to obtain a yellow oil compound (98%).

$^1$H NMR (C$_6$D$_6$): δ 0.75 (d, J=6.8 Hz, 3H, CH$_3$), 1.11-1.25 (m, 4H, Cy), 1.42-1.47 (m, 2H, Cy), 1.56-1.62 (m, 2H, Cy), 1.61 (s, 3H, CH$_3$), 1.87 (dd, J=2.0, 18.4 Hz, 1H, CH$_2$), 1.97-2.06 (m, 2H, Cy), 2.16-2.26 (m, 1H, CH), 2.46 (dd, J=6.4, 18.4 Hz, 1H, CH$_2$), 3.17-3.29 (m, 1H, N—CH), 4.14 (br s, 1H, NH), 6.79 (d, J=8.0 Hz, 1H, C$_6$H$_3$), 7.14 (tt, J=1.2, 7.2 Hz, 1H, C$_6$H$_5$), 7.27 (t, J=8.0 Hz, 2H, C$_6$H$_5$), 7.36 (d, J=2.0 Hz, 1H, C$_6$H$_3$), 7.55 (dd, J=2.0, 8.4 Hz, 1H, C$_6$H$_3$), 7.62 (dd, J=1.2, 8.0 Hz, 2H, C$_6$H$_5$) ppm. $^{13}$C {$^1$H} NMR (C$_6$D$_6$): δ 16.19, 19.39, 25.23, 26.45, 33.59, 37.80, 43.73, 51.81, 112.53, 119.36, 126.29, 126.76, 128.18, 129.02, 129.81, 130.25, 141.92, 145.76, 177.41, 205.30 ppm

Example 14

2-(4-Chloro-2-Cyclohexylaminophenyl)-3,4-dimethyl-2-cyclopenten-1-one

The same procedure was carried out in the same manner as in Example 11 except that 4-chloro-N-cyclohexylaniline was used instead of 2-bromo-N-cyclohexylaniline to obtain a yellow oil compound (97%).

$^1$H NMR (C$_6$D$_6$): δ 0.68 (d, J=7.2 Hz, 3H, CH$_3$), 1.03-1.17 (m, 4H, Cy), 1.40-1.46 (m, 2H, Cy), 1.47 (s, 3H, CH$_3$), 1.53-1.55 (m, 2H, Cy), 1.78 (dd, J=2.0, 18.4 Hz, 1H, CH$_2$), 1.84-1.94 (m, 2H, Cy), 2.08-2.12 (m, 1H, CH), 2.36 (dd, J=7.2, 18.4 Hz, 1H, CH$_2$), 2.97-3.08 (m, 1H, N—CH), 4.00 (br s, 1H, NH), 6.47 (d, J=8.8 Hz, 1H, C$_6$H$_3$), 7.01 (d, J=2.4 Hz, 1H, C$_6$H$_3$), 7.21 (dd, J=2.4, 8.8 Hz, 1H, C$_6$H$_3$) ppm. $^{13}$C {$^1$H}NMR (C$_6$D$_6$): δ 16.02, 19.30, 21.15, 26.37, 33.32, 37.80, 43.61, 51.76, 113.08, 120.46, 120.98, 129.05, 130.94, 138.63, 144.87, 178.02, 204.82 ppm

Example 15

2-(2-Cyclohexylamino-4-fluorophenyl)-3,4-dimethyl-2-cyclopenten-1-one

The same procedure was carried out in the same manner as in Example 11 except that N-cyclohexyl-4-fluoroaniline was used instead of 2-bromo-N-cyclohexylaniline to obtain a yellow oil compound (90%).

$^1$H NMR (C$_6$D$_6$): δ 0.76 (d, J=7.2 Hz, 3H, CH$_3$), 1.06-1.20 (m, 4H, Cy), 1.43-1.48 (m, 2H, Cy), 1.56 (s, 3H, CH$_3$), 1.54-1.62 (m, 2H, Cy), 1.81 (dd, J=2.0, 18.4 Hz, 1H, CH$_2$), 1.86-1.96 (m, 2H, Cy), 2.18-2.22 (m, 1H, CH), 2.40 (dd, J=6.8, 18.4 Hz, 1H, CH$_2$), 2.99-3.08 (m, 1H, N—CH), 3.78 (br s, 1H, NH), 6.48 (dd, J=4.8, 8.8 Hz, 1H, C$_6$H$_3$), 6.77 (dd, J=3.2, 8.8 Hz, 1H, C$_6$H$_3$), 6.91 (td, J=3.2, 8.8 Hz, 1H, C$_6$H$_3$) ppm. $^{13}$C {$^1$H} NMR (C$_6$D$_6$): δ 16.06, 19.30, 25.24, 26.45, 33.53, 37.77, 43.63, 52.21, 112.81 (d, J$_{CF}$=7.6 Hz, C$_6$H$_3$), 115.51 (d, $^2$J$_{CF}$=21.2 Hz, C$_6$H$_3$), 117.84 (d, $^2$J$_{CF}$=21.2 Hz, C$_6$H$_3$), 120.15 (d, J$_{CF}$=7.6 Hz, C$_6$H$_3$), 142.66, 154.01, 156.33, 177.80, 204.84 ppm

Example 16

2-(2,3,5-trimethylcyclopenta-1,4-dienyl)phenyl-N-cyclohexylamine

Into a 150-mL flask, CeCl$_3$ (5.27 g, 21.4 mmol) and THF (24 mL) were put, the temperature was lowered to −78° C., and then MeLi (1.6 M in diethyl ether, 13.4 mL, 21.4 mmol) was added to the mixture. If the color of the solution turned yellow, after 1 hour, 2-(2-aminophenyl)-3,4-dimethyl-2-cyclopenten-1-one (2.02 g, 7.13 mmol) was added to the flask, and the mixture was stirred for 2 hours at −78° C. Then, to the flask, distilled water (20 mL) and E.A (40 mL) were added to thereto, and the solution was transferred to a separatory funnel to extract an organic layer. Further, EA (10 mL) was further added to perform extraction twice, and the organic layer was combined. To the combined organic layer, an aqueous HCL solution (2 N, 20 mL) was added, and vigorously shaken for 2 minutes. The organic layer was neutralized with NaHCO$_3$ (4 mL), and then the organic layer was combined, and the remaining water was removed over MgSO$_4$. The glass filter was used to remove CeCl$_3$ and MgSO$_4$, and a rotary evaporator was used to remove the solvent. The remaining compound was separated by column chromatography (hexane:E.A=10:1) to obtain a pure final product (1.66 g, 83%).

$^1$H NMR (CDCl$_3$): δ 1.06-1.20 (m, 2H, Cy), 1.21-1.30 (m, 1H, Cy), 1.34-1.46 (m, 2H, Cy), 1.68 (d, J=1.2 Hz, 3H, CH$_3$), 1.74-1.81 (m, 3H, Cy), 1.87 (s, 3H, CH$_3$), 2.01 (s, 3H, CH$_3$), 2.03-2.10 (m, 2H, Cy), 2.94 (AB, J=22.8H$_z$, 1H, CH$_2$), 3.01 (AB, J=22.8H$_z$, 1H, CH$_2$), 3.29-3.34 (m, 1H, N—CH), 3.67 (br s, 1H, NH), 6.69 (td, J=1.2, 7.2 Hz, 1H, C$_6$H$_4$), 6.71 (d, J=8.0 Hz, 1H, C$_6$H$_4$), 6.93 (dd, J=1.6, 7.2 Hz, 1H, C$_6$H$_4$), 7.20 (ddd, J=1.6, 7.2, 8.0 Hz, 1H, C$_6$H$_4$) ppm. $^{13}$C {$^1$H} NMR (CDC$_3$): δ 11.70, 13.73, 14.47, 25.13, 25.17, 26.05, 33.17, 33.50, 48.81, 51.50, 110.18, 115.50, 122.53, 127.76, 130.01, 133.11, 135.64, 136.80, 139.66, 144.86 ppm

Example 17

4-Methyl-2-(2,3,5-trimethylcyclopenta-1,4-dienyl) phenyl-N-cyclohexylamine

The same procedure was carried out in the same manner as in Example 16 except that 2-(2-cyclohexylamino-4-methylphenyl)-3,4-dimethyl-2-cyclopenten-1-one was used instead of 2-(2-aminophenyl)-3,4-dimethyl-2-cyclopenten-1-one to obtain a yellow solid compound (70%).

$^1$H NMR (C$_6$D$_6$): δ 0.92-1.04 (m, 3H, Cy), 1.12-1.22 (m, 2H, Cy), 1.40-1.48 (m, 1H, Cy), 1.50-1.57 (m, 2H, Cy), 1.81 (s, 3H, CH$_3$), 1.88 (s, 3H, CH$_3$), 1.90 (s, 3H, CH$_3$), 1.93-2.01 (m, 2H, Cy), 2.28 (s, 3H, CH$_3$), 2.72 (AB, J=22.8 H$_z$, 1H, CH$_2$), 2.80 (AB, J=22.8H$_z$, 1H, CH$_2$), 3.16-3.25 (m, 1H, N—CH), 3.65 (br d, J=8.0 Hz, 1H, NH), 6.70 (d, J=8.0 Hz, 1H, C$_6$H$_3$), 6.93 (d, J=2.0 Hz, 1H, C$_6$H$_3$), 7.07 (dd, J=2.0, 8.0 Hz, 1H, C$_6$H$_3$) ppm

Example 18

4-Chloro-2-(2,3,5-trimethylcyclopenta-1,4-dienyl)phenyl-N-cyclohexylamine

The same procedure was carried out in the same manner as in Example 16 except that 2-(4-chloro-2-cyclohexylaminophenyl)-3,4-dimethyl-2-cyclopenten-1-one was used instead of 2-(2-aminophenyl)-3,4-dimethyl-2-cyclopenten-1-one to obtain a yellow oil compound (75%).

$^1$H NMR (C$_6$D6$_6$): δ 0.87-1.04 (m, 3H, Cy), 1.11-1.23 (m, 2H, Cy), 1.41-1.47 (m, 1H, Cy), 1.50-1.58 (m, 2H, Cy), 1.80 (s, 3H, CH$_3$), 1.88 (s, 3H, CH$_3$), 1.90 (s, 3H, CH$_3$), 1.93-2.00 (m, 2H, Cy), 2.72 (AB, J=22.8H$_z$, 1H, CH$_2$), 2.80 (AB, J=22.8H$_z$, 1H, CH$_2$), 3.17-3.28 (m, 1H, N—CH), 3.86 (br d, J=8.0 Hz, 1H, NH), 6.77 (d, J=8.0 Hz, 1H, C$_6$H$_3$), 7.13 (t, J=8.0 Hz, 1H, C$_6$H$_5$), 7.27 (t, J=8.0 Hz, 2H, C$_6$H$_5$), 7.48 (d, J=2.4 Hz, 1H, C$_6$H$_3$), 7.59 (dd, J=2.4, 8.0 Hz, 1H, C$_6$H$_3$), 7.64 (d, J=8.0 Hz, 2H, C$_6$H$_5$) ppm. $^{13}$C {$^1$H} NMR (C$_6$D$_6$): δ 12.21, 13.90, 14.78, 25.42, 25.45, 26.35, 33.78, 33.81, 49.13, 51.67, 111.22, 123.43, 126.09, 126.60, 127.22, 128.98, 129.23, 129.35, 133.45, 136.29, 137.15, 140.73, 142.05, 145.00 ppm

Example 19

4-Fluoro-2-(2,3,5-trimethylcyclopenta-1,4-dienyl)phenyl-N-cyclohexylamine

The same procedure was carried out in the same manner as in Example 16 except that 2-(4-fluoro-2-cyclohexylaminophenyl)-3,4-dimethyl-2-cyclopenten-1-one was used instead of 2-(2-aminophenyl)-3,4-dimethyl-2-cyclopenten-1-one to obtain a yellow solid compound (60%).

$^1$H NMR (C$_6$D$_6$): δ 0.80-0.90 (m, 2H, Cy), 0.94-1.01 (m, 1H, Cy), 1.08-1.18 (m, 3H, Cy), 1.40-1.51 (m, 4H, Cy), 1.67 (s, 3H, CH$_3$), 1.77 (s, 3H, CH$_3$), 1.83 (s, 3H, CH$_3$), 2.61 (AB, J=22.8H$_z$, 1H, CH$_2$), 2.71 (AB, J=22.8H$_z$, 1H, CH$_2$), 2.99-3.07 (m, 1H, N—CH), 3.68 (br d, J=8.0 Hz, 1H, NH), 6.44 (d, J=8.8 Hz, 1H, C$_6$H$_3$), 7.07 (d, J=2.4 Hz, 1H, C$_6$H$_3$), 7.17 (dd, J=2.4, 8.8 Hz, 1H, C$_6$H$_3$) ppm, $^{13}$C {$^1$H} NMR (C$_6$D$_6$): δ 11.93, 13.82, 14.54, 25.36, 25.39, 26.29, 33.56, 33.59, 49.10, 51.65, 111.77, 120.79, 124.66, 128.24, 130.18, 133.70, 135.67, 137.73, 139.52, 144.15 ppm

Example 20

Phenylene (N-cyclohexylamido)(2,3,5-trimethylcyclopentadienyl)titanium dichloride To a 25-mL flask, 2-(2,3,5-trimethylcyclopenta-1,4-dienyl)phenyl-N-cyclohexylamine (0.196 g, 0.696 mmol) and Ti(N(Me)$_2$)$_4$ (0.156 g, 0.696 mmol), which had been diluted with toluene (2 mL), were put. The solution was subject to reaction for 2 days under heating to 80° C., and then the solvent was removed to obtain a red solid. To the obtained solid, toluene (2 mL) and Me$_2$SiCl$_2$(0.269 g, 2.09 mmol) was successively added at normal temperature, and stirred for 4 hours at normal temperature, and then the solvent was removed. Then, the solid was recrystallized from hexane at −30° C. to obtain a red solid as a final product (0.183 g, 66%).

$^1$H NMR (C$_6$D$_6$): δ 0.83-1.00 (m, 2H, Cy), 1.35-1.51 (m, 3H, Cy), 1.64 (s, 3H, CH$_3$), 1.66-1.74 (m, 3H, Cy), 1.75 (s, 3H, CH$_3$), 1.81-1.95 (m, 2H, Cy), 2.09 (s, 3H, CH$_3$), 5.46-5.58 (m, 1H, N—CH), 6.06 (s, 1H, Cp-H), 6.65 (d, J=7.2 Hz, 1H, C$_6$H$_4$), 6.95 (td, J=0.8, 7.2 Hz, 1H, C$_6$H$_4$), 7.07 (dd, J=2.0, 7.2 Hz, 1H, C$_6$H$_4$), 7.11 (td, J=2.0, 7.2 Hz, 1H, C$_6$H$_4$) ppm. $^{13}$C {$^1$H} NMR (C$_6$D$_6$): δ 12.38, 14.48, 14.82, 25.81, 27.08, 27.51, 59.57, 111.11, 118.50, 123.05, 128.49, 128.99, 131.56, 132.17, 142.13, 142.93, 143.42, 164.02 ppm. Anal. Calc. (C$_{20}$H$_{25}$Cl$_2$NTi): C, 60.33; H, 6.33; N, 3.52%. Found: C, 60.19; H, 6.52; N, 3.29%.

Example 21

4-Methylphenylene (N-cyclohexylamido)(2,3,5-trimethylcyclopentadienyl)titanium dichloride The same procedure was carried out in the same manner as in Example 20 except that 4-methyl-2-(2,3,5-trimethylcyclopenta-1,4-dienyl)phenyl-N-cyclohexylamine was used instead of 2-(2,3,5-trimethylcyclopenta-1,4-dienyl)phenyl-N-cyclohexylamine to obtain a red solid compound (59%).

$^1$H NMR (C$_6$D$_6$): δ 0.84-1.00 (m, 2H, Cy), 1.37-1.53 (m, 3H, Cy), 1.69 (s, 3H, CH$_3$), 1.71-1.76 (m, 2H, Cy), 1.80 (s, 3H, CH$_3$), 1.85-1.97 (m, 2H, Cy), 2.10-2.18 (m, 1H, Cy), 2.11 (s, 3H, CH$_3$), 2.21 (s, 3H, CH$_3$), 5.57 (m, 1H, N—CH), 6.09 (s, 1H, Cp-H), 6.60 (d, J=8.4 Hz, 1H, C$_6$H$_3$), 6.91 (s, 1H, C$_6$H$_3$), 6.94 (d, J=8.4 Hz, 1H, C$_6$H$_3$) ppm. $^{13}$C {$^1$H} NMR (C$_6$D$_6$): δ 12.45, 14.50, 14.89, 20.69, 25.85, 27.10, 27.58, 59.59, 110.77, 118.38, 128.87, 129.68, 131.37, 132.55, 132.75, 142.06, 142.64, 143.11, 161.82 ppm. Anal. Calc. (C$_{21}$H$_{27}$Cl$_2$NTi): C, 61.19; H, 6.60; N, 3.40%. Found: C, 60.94; H, 6.54; N, 3.61%.

Example 22

4-Phenylphenylene (N-cyclohexylamido)(2,3,5-trimethylcyclopentadienyl)titanium dichloride The same procedure was carried out in the same manner as in Example 20 except that 4-phenyl-2-(2,3,5-trimethylcyclopenta-1,4-dienyl)phenyl-N-cyclohexylamine was used instead of 2-(2,3,5-trimethylcyclopenta-1,4-dienyl)phenyl-N-cyclohexylamine to obtain a red solid compound (87%).

$^1$H NMR (C$_6$D$_6$): δ 0.93-1.06 (m, 2H, Cy), 1.38-1.56 (m, 4H, Cy), 1.70 (s, 3H, CH$_3$), 1.72-1.80 (m, 2H, Cy), 1.81 (s, 3H, CH$_3$), 1.88-2.03 (m, 2H, Cy), 2.13 (s, 3H, CH$_3$), 5.54 (m, 1H, N—CH), 6.10 (s, 1H, Cp-H), 6.71 (d, J=8.0 Hz, 1H, C$_6$H$_3$), 7.20 (d, J=8.0 Hz, 1H, C$_6$H$_5$), 7.31 (t, J=8.0 Hz, 2H, C$_6$H$_5$), 7.38 (d, J=2.0 Hz, 1H, C$_6$H$_3$), 7.44 (dd, J=2.0, 8.0 Hz, 1H, C$_6$H$_3$), 7.58 (dd, J=2.0, 8.0 Hz, 2H, C$_6$H$_5$) ppm. $^{13}$C {$^1$H} NMR (C$_6$D$_6$): δ 12.58, 14.63, 15.03, 25.95, 27.17, 27.68, 59.73, 111.22, 118.40, 126.81, 126.99, 127.27, 128.79, 129.05, 131.50, 132.68, 136.14, 140.46, 141.77, 142.72, 143.20, 163.14 ppm. Anal. Calc. (C$_{26}$H$_{29}$C$_2$NTi): C, 65.84; H, 6.16; N, 2.95%. Found: C, 65.92; H, 6.05; N, 3.13%.

Example 23

4-Chlorophenylene (N-cyclohexylamido)(2,3,5-trimethylcyclopentadienyl) titanium dichloride The same procedure was carried out in the same manner as in Example 20 except that 4-chloro-2-(2,3,5-trimethylcyclopenta-1,4-dienyl)phenyl-N-cyclohexylamine was used instead of 2-(2,3,5-trimethylcyclopenta-1,4-dienyl)phenyl-N-cyclohexylamine to obtain a red solid compound (73%).

$^1$H NMR ($C_6D_6$): δ 0.82-0.96 (m, 2H, Cy), 1.31-1.50 (m, 4H, Cy), 1.56 (s, 3H, $CH_3$), 1.67 (s, 3H, $CH_3$), 1.68-1.78 (m, 2H, Cy), 1.91-2.03 (m, 2H, Cy), 2.04 (s, 3H, $CH_3$), 5.39 (m, 1H, N—CH), 6.00 (s, 1H, Cp-H), 6.40 (d, J=8.8 Hz, 1H, $C_6H_3$), 7.04 (d, J=2.8 Hz, 1H, $C_6H_3$), 7.10 (dd, J=2.8, 8.8 Hz, 1H, $C_6H_3$) ppm. $^{13}$C {$^1$H} NMR ($C_6D_6$): δ 12.30, 14.44, 14.74, 25.72, 26.97, 27.28, 59.67, 111.71, 118.64, 128.33, 128.45, 129.05, 131.85, 133.38, 140.29, 142.78, 143.28, 162.54 ppm. Anal. Calc. ($C_{20}H_{24}Cl_3NTi$): C, 55.52; H, 5.59; N, 3.24%. Found: C, 55.38; H, 5.79; N, 3.34%

Example 24

4-Fluorophenylene (N-cyclohexylamido)(2,3,5-trimethylcyclopentadienyl) titanium dichloride The same procedure was carried out in the same manner as in Example 20 except that 4-fluoro-2-(2,3,5-trimethylcyclopenta-1,4-dienyl)phenyl-N-cyclohexylamine was used instead of 2-(2,3,5-trimethylcyclopenta-1,4-dienyl)phenyl-N-cyclohexylamine to obtain a red solid compound (90%).

$^1$H NMR ($C_6D_6$): δ 0.88-1.03 (m, 2H, Cy), 1.32-1.47 (m, 2H, Cy), 1.47-1.56 (m, 1H, Cy), 1.61 (s, 3H, $CH_3$), 1.71 (s, 3H, $CH_3$), 1.72-1.84 (m, 3H, Cy), 1.93-2.05 (m, 2H, Cy), 2.09 (s, 3H, $CH_3$), 5.38-5.47 (m, 1H, N—CH), 6.05 (s, 1H, Cp-H), 6.43 (dd, J=4.8, 8.8 Hz, 1H, $C_6H_3$), 6.79-6.85 (m, 2H, $C_6H_3$) ppm. $^{13}$C {$^1$H} NMR ($C_6D_6$): δ 12.61, 14.75, 15.04, 26.03, 27.29, 27.58, 27.66, 59.74, 111.38 (d, $3J_{CF}$=8.3 Hz, $C_6H_3$), 114.80 (d, $2J_{CF}$=22.8 Hz, $C_6H_3$), 116.49 (d, $2J_{CF}$=23.5 Hz, $C_6H_3$), 118.62, 131.69, 133.42 (d, $3J_{CF}$=8.3 Hz, $C_6H_3$), 140.02, 142.53, 143.00, 159.74 (d, $1J_{CF}$=240.4 Hz, $C_6H_3$), 160.02 ppm. $^{19}$F NMR ($C_6D_6$): δ-28.83 (dd, J=7.8, 12.4 Hz) ppm.

Example 25

4-(4-(cyclohexylamino)benzyl)-N-cyclohexylbenzeneamine

To a 250-mL flask, 4,4-methyleneaniline (4.000 g, 20.175 mmol), cyclohexanone (15.839 g, 161.396 mmol), molecular sieves (4 Å, 10.0 g) and toluene (30 mL) as a solvent were put. The solution was subject to reaction at 100° C. for 2 days. After reaction, the solution was cooled to room temperature, the molecular sieves were filtered out, and dried in vacuo at 60° C. to obtain 4-(4-(cyclohexylideneamino)benzyl)-N-cyclohexylbenzeneamine. The obtained compound was dissolved in methanol (60 mL), sodium borohydride (4.576 g, 121.047 mmol) was added thereto, and the mixture was reacted at room temperature for 2 hours. Thereafter, the reaction solution was neutralized with a 1 N KOH (80 mL) solution. The neutralized solution was transferred to a separatory funnel and the organic layer was extracted from M.C. (methylenechloride) (60 mL) twice. The combined organic layer was dried over $MgSO_4$, and then recrystallized from hexane and ethyl acetate solvent (v/v=20:1) to obtain a white solid compound (3.765 g, 51%).

$^1$H NMR ($CDCl_3$): 6.94 (d, 4H, Ph), Ph), 3.72 (s, 2H, $CH_2$), 3.37 (s, 2H, NH), 3.19 (m, 2H, $CH^{Cy}$), 2.02 (m, 4H, $CH_2^{Cy}$), 1.72 (m, 4H, $CH_2^{Cy}$), 1.57 (m, 2H, $CH_2^{Cy}$), 1.33 (m, 4H, $CH_2^{Cy}$), 1.21 (m, 2H, $CH_2^{Cy}$) 1.12 (m, 4H, $CH_2^{Cy}$)

Example 26

4-(3-Bromo-4-(cyclohexylamino)benzyl)-2-bromo-N-cyclohexylbenzeneamine

In a 100-mL flask, 4-(4-(cyclohexylamino)benzyl)-N-cyclohexylbenzeneamine (1.
5 g, 4.137 mmol) was dissolved in M.C. (15 mL), and the solution was cooled to 0° C. To the flask, a Br (1.322 mL, 8.275 mmol) solution in M.C. (10 mL) was slowly added at 0° C. for 30 minutes and subject to reaction for 2 hours. Thereafter, the reaction solution was neutralized with a 1 N KOH (10 mL) solution. The neutralized solution was transferred to a separatory funnel and the organic layer was extracted from M.C. (40 mL) twice. The combined organic layer was dried over $MgSO_4$, and then purified by column chromatography using hexane and ethyl acetate solvent (v/v=20:1) to obtain a white solid compound (1.523 g, 71%).

$^1$H NMR ($C_6D_6$): 7.35 (d, 2H, Ph), 6.89 (dd, 2H, Ph), 6.45 (d, 2H, Ph), 4.22 (d, 2H, NH), 3.54 (s, 2H, CH2), 3.04 (m, 2H, $CH^{Cy}$), 1.80 (m, 4H, $CH_2^{Cy}$), 1.52 (m, 4H, $CH_2^{Cy}$), 1.41 (m, 2H, $CH_2^{Cy}$), 1.16-0.93 (m, 10H, $CH_2^{Cy}$). $^{13}$C NMR ($C_6D_6$): 142.74, 133.04, 130.86, 129.14, 112.29, 110.28, 51.81, 39.78, 33.31, 26.25, 25.17

Example 27

4-(3-(3,4-Dimethylcyclopenta-1,3-dienone)-4-(cyclohexylamino)benzyl)-2-(3,4-di methylcyclopenta-1,3-dienone)-N-cyclohexylbenzeneamine Boronic acid (0.857 g, 5.565 mmol), $Na_2CO_3$ (0.843 g, 7.951 mmol), $Pd(P(Ph)_3)_4$ (0.123 g, 0.106 mmol) and the compound prepared in Example 26 (1.378 g, 2.650 mmol) were dissolved in DME (12 mL) and water (4 mL), and the solution was subject to reaction at 95° C. for 40 hours. The reaction solution was cooled to room temperature, and then the organic layer was extracted from ethyl acetate (30 mL). The obtained, extracted solution was dried over $MgSO_4$, and then purified by column chromatography using hexane and ethyl acetate (3:1) solvent to obtain a yellow solid compound (1.206 g, 79%).

$^1$H NMR ($CDCl_3$): 6.96 (dd, 2H, Ph), 6.64 (d, 2H, Ph), 6.60 (d, 2H, Ph), 3.73 (s, 2H, $CH_2$), 3.32 (s, 2H, NH), 3.19 (m, 2H, $CH^{Cy}$), 2.87 (m, 2H, CH), 2.74 (dd, 2H, $CH_2$), 2.11 (dd, 2H, $CH_2$), 1.95 (m, 4H, $CH_2^{Cy}$), 1.93 (s, 6H, Me), 1.67 (m, 4H, $CH_2^{Cy}$), 1.57 (m, 2H, $CH_2^{Cy}$), 1.36-1.03 (m, 10H, $CH_2^{Cy}$), 1.25 (d, 6H, Me).

Example 28

4-(3-(2,3,5-Trimethylcyclopenta-1,3-diene)-4-(cyclohexylamino)benzyl)-2-(2,3,5-trimethylcyclopenta-1,3-diene)-N-cyclohexylbenzeneamine Anhydrous $CeCl_3$ (3.744 g, 15.203 mmol) was dissolved in THF (30 mL), and the solution was cooled to −78° C. To the solution, MeLi (9.502 mL, 15.203 mmol) was slowly added, and then subject to reaction at −78° C. for 1 hour. The compound (4-(3-(3,4-dimethylcyclopenta-1,3-dienone)-4-(cyclohexylamino)benzyl)-2-(3,4-dimethylcyclopenta-1,3-dienone)-N-cyclohexylbenzeneamine) (1.100 g, 1.900 mmol) was added thereto, and then further subject to reaction at −78° C. for 2 hours. To the solution, distilled water (30 mL) and ethyl acetate (40 mL) were added to extract the organic layer. To the extracted organic layer, 2 N HCl was added, and subject to reaction for 2 minutes. The resultant was neutralized with a NaHCO$_3$ base, and the obtained organic layer was dried over MgSO$_4$. The obtained oil was purified by column chromatography using hexane and ethyl acetate (v/v, 20:1) solvent to obtain a white oil (0.502 g, 46%).

$^1$H NMR (CDCl$_3$): 6.95 (dd, 2H, Ph), 6.70 (d, 2H, Ph), 6.55 (d, 2H, Ph), 3.74 (s, 2H, CH$_2$), 3.43 (d, 2H, NH), 3.20 (m, 2H, CH$^{Cy}$), 2.86 (qd, 4H, CH$_2$), 1.96 (m, 4H, CH$_2^{Cy}$), 1.91 (s, 6H, Me), 1.76 (s, 6H, Me), 1.70-1.54 (m, 6H, CH$_2^{Cy}$), 1.54 (s, 6H, Me), 1.30 (m, 4H, CH$_2^{Cy}$), 1.16 (m, 2H, CH$_2^{Cy}$), 1.01 (m, 4H, CH$_2^{Cy}$).

Example 29

Methylidene-bis-(3,4-phenylene (cyclohexylamido) (2,3,5-Trimethylcyclopentadienyl)titanium dichloride A solution containing 4-(3-(2,3,5-trimethylcyclopenta-1, 3-diene)-4-(cyclohexylamino)benzyl)-2-(2,3,5-trimethylcyclopenta-1,3-diene)-N-cyclohexylbenzeneamine (1.1481 g, 2.58 mmol), Ti(N(Me$_2$))$_4$ (1.271 g, 5.67 mmol) and toluene (15 mL) was subject to reaction at 80° C. for 2 days. Then, the solvent was removed from the solution, and the resultant was extracted from pentane to obtain a red solid. The solid compound was dissolved in toluene (15 mL), and Me$_2$SiCl$_2$ (1.996 g, 15.46 mmol) was added to the solution. Then, the solution was stirred at normal temperature for 4 hours, and the solvent was removed therefrom. To the resultant, pentane was added and the mixture was pulverized and filtered to obtain a red solid compound (1.808 g, overall 87%).

$^1$H NMR (C$_6$D$_6$): δ 0.91-0.97 (m, 2H, Cy-CH$_2$), 1.40-1.52 (m, 6H, Cy-CH$_2$), 1.68-1.75 (m, 3H, Cy-CH$_2$), 1.70 (s, 6H, CH$_3$), 1.82 (s, 6H, CH$_3$), 1.89-2.00 (m, 6H, Cy-CH$_2$), 2.06-2.18 (m, 3H, Cy-CH$_2$), 2.13 (s, 6H, CH$_3$), 3.95 (s, 2H, bridged-CH$_2$), 5.50-5.61 (m, 2H, N—CH), 6.10 (s, 2H, Cp-H), 6.68 (d, J=8.0 Hz, 2H, C$_6$H$_3$—CH), 7.04 (s, 2H, C$_6$H$_3$—CH), 7.09 (d, J=8.0 Hz, 2H, C$_6$H$_3$—CH) ppm, $^{13}$C {$^1$H} NMR (C$_6$D$_6$): δ 12.76, 44.80, 15.17, 26.09, 27.36, 27.88, 27.95, 59.87, 110.94, 118.52, 128.87, 129.53, 131.59, 132.76, 136.41, 141.80, 142.57, 143.03, 162.45 ppm.

Comparative Example 1

2-Bromo-N-3-pentylaniline

The same procedure was carried out as in Example 2 except that 4-bromoaniline and 3-pentanone were used instead of 2-bromoaniline and cyclohexanone to obtain a colorless oil compound (61%).

$^1$H NMR (CDCl$_3$): δ 1.01 (t, J=7.6 Hz, 6H, CH$_3$), 1.54-1.74 (m, 4H, CH$_2$), 3.34 (quintet, J=6.0 Hz, 1H, N—CH), 4.25 (s, 1H, NH), 6.56 (td, J=7.6, 1.2 Hz, 1H, C$_6$H$_4$), 6.67 (dd, J=8.0, 1.2 Hz, 1H, C$_6$H$_4$), 7.18 (td, J=7.6, 1.6 Hz, 1H, C$_6$H$_4$), 7.45 (dd, J 8.0, 1.6 Hz, 1H, C$_6$H$_4$) ppm Comparative Example 2

2-(2-ethylpropylamino-4-methylphenyl)-3,4-dimethyl-2-cyclopenten-1-one

The same procedure was carried out as in Example 11 except that 2-bromo-N-3-pentylaniline was used instead of 2-bromo-N-cyclohexylaniline to obtain a yellow oil compound (88%).

$^1$H NMR (CDCl$_3$): δ 0.91 (t, J=7.6 Hz, 6H, CH$_3$), 1.32 (d, J=7.6 Hz, 3H, CH$_3$), 1.43-1.61 (m, 4H, CH$_2$), 2.02 (s, 3H, CH$_3$), 2.19 (dd, J=18.4, 2.0 Hz, 1H, CH$_2$), 2.83 (dd, J=18.4, 6.8 Hz, 1H, CH$_2$), 2.95 (br quintet, J=6.8 Hz, 1H, CH), 3.25 (quintet, J=5.6 Hz, 1H, N—CH), 3.34 (s, 1H, NH), 6.67 (d, J=7.6 Hz, 1H, C$_6$H$_4$), 6.68 (t, J=7.6 Hz, 1H, C$_6$H$_4$), 6.86 (d, J=6.4 Hz, 1H, C$_6$H$_4$), 7.12 (td, J=1.2, 7.6 Hz, 1H, C$_6$H$_4$) ppm Comparative Example 3

2-(2,3,5-Trimethylcyclopenta-1,4-dienyl)phenyl-N-ethylpropylamine

The same procedure was carried out as in Example 16 except that 2-(2-ethylpropylamino-4-methylphenyl)-3,4-dimethyl-2-cyclopenten-1-one was used instead of 2-(2-aminophenyl)-3,4-dimethyl-2-cyclopenten-1-one to obtain a colorless oil compound (60%).

$^1$H NMR (CDCl$_3$): δ 0.91 (t, J=7.6 Hz, 6H, CH$_3$), 1.45-1.63 (m, 4H, CH$_2$), 1.68 (s, 3H, CH$_3$), 1.87 (s, 3H, CH$_3$), 2.01 (s, 3H, CH$_3$), 2.95 (AB, J=22.4 Hz, 1H, CH$_2$), 3.02 (AB, J=22.4 Hz, 1H, CH$_2$), 3.30 (br quintet, J=6.0 Hz, 1H, N—CH), 3.56 (br s, 1H, NH), 6.67 (d, J=7.6H$_2$, 1H, C$_6$H$_4$), 6.68 (t, J=7.6 Hz, 1H, C$_6$H$_4$), 6.92 (dd, J=1.6, 7.6 Hz, 1H, C$_6$H$_4$), 7.20 (td, J=1.6, 7.6 Hz, 1H, C$_6$H$_4$) ppm Comparative Example 4

Phenylene (N-ethylpropylamido)(2,3,5-trimethylcyclopentadienyl)titanium dichloride The same procedure was carried out as in Example 20 except that 2-(2,3,5-trimethylcyclopenta-1,4-dienyl)phenyl-N-ethylpropylamine was used instead of 2-(2,3,5-trimethylcyclopenta-1,4-dienyl)phenyl-N-cyclohexylamine to obtain a red solid compound (67%).

$^1$H NMR (C$_6$D$_6$): δ 1.01 (t, J=7.6 Hz, 6H, pentyl-CH$_3$), 1.66 (s, 3H, CH$_3$), 1.78 (s, 3H, CH$_3$), 1.79-1.93 (m, 4H, pentyl-CH$_2$), 2.10 (s, 3H, CH$_3$), 5.43-5.50 (m, 1H, pentyl-CH), 6.07 (s, 1H, Cp-H), 6.43 (d, J=8.0 Hz, 1H, C$_6$H$_4$—CH), 6.95 (t, J=8.0 Hz, 1H, C$_6$H$_4$—CH), 7.07 (d, J=8.0 Hz, 1H, C$_6$H$_4$), 7.08 (t, J=8.0 Hz, 1H, C$_6$H$_4$) ppm Comparative Example 5

2-(2-t-Butylamino-4-methylphenyl)-3,4-dimethyl-2-cyclopenten-1-one

The same procedure was carried out as in Example 11 except that 2-bromo-N-t-butylaniline was used instead of 2-bromo-N-cyclohexylaniline to obtain a yellow oil compound (96%).

$^1$H NMR (CDCl$_3$): δ 1.30 (d, J=6.8 Hz, 3H, CH$_3$), 1.31 (s, 9H, C(CH$_3$)$_3$), 2.01 (s, 3H, CH$_3$), 2.17 (dd, J=2.0, 18.4 Hz, 1H, CH$_2$), 2.80 (dd, J=6.4, 18.4 Hz, 1H, CH$_2$), 2.93 (br quintet, J=6.4 Hz, 1H, CH), 3.44 (s, 1H, NH), 6.75 (td, J=1.2, 7.2 Hz, 1H, C$_6$H$_4$), 6.87 (d, J=6.8 Hz, 1H, C$_6$H$_4$), 6.98 (d, J=8.4 Hz, 1H, C$_6$H$_4$) 7.17 (td, J=1.6, 7.6 Hz, 1H, C$_6$H$_4$) ppm Comparative Example 6

2-(2,3,5-Trimethylcyclopenta-1,4-dienyl)phenyl-N-t-butylamine

The same procedure was carried out as in Example 16 except that 2-(2-t-butylamino-4-methylphenyl)-3,4-dimethyl-2-cyclopenten-1-one was used instead of 2-(2-aminophenyl)-3,4-dimethyl-2-cyclopenten-1-one to obtain a colorless oil (58%).

$^1$H NMR (CDCl$_3$): δ 1.37 (s, 9H, C(CH$_3$)$_3$), 1.71 (s, 3H, CH$_3$), 1.90 (s, 3H, CH$_3$), 2.03 (s, 3H, CH$_3$), 2.96 (AB, J=22.8H$_z$, 1H, CH$_2$), 3.03 (AB, J=22.8H$_z$, 1H, CH$_2$), 3.83 (br s, 1H, NH), 6.77 (t, J=7.2 Hz, 1H, C$_6$H$_4$), 6.97 (d, J=7.6 Hz, 1H, C$_6$H$_4$), 7.01 (d, J=8.0 Hz, 1H, C$_6$H$_4$), 7.21 (t, J=7.2 Hz, 1H, C$_6$H$_4$) ppm Comparative Example 7

Phenylene (N-t-butylamido)(2,3,5-trimethylcyclopentadienyl)titanium dichloride

The same procedure was carried out as in Example 20 except 2-(2,3,5-trimethylcyclopenta-1,4-dienyl)phenyl-N-t-butylamine was used instead of 2-(2,3,5-trimethylcyclopenta-1,4-dienyl)phenyl-N-cyclohexylamine and reaction was performed at 80° C. for 10 days, to obtain a product (56%).

$^1$H NMR (C$_6$D$_6$): δ 1.68 (s, 3H, CH$_3$), 1.80 (s, 12H, C(CH$_3$)$_3$ and CH$_3$), 2.12 (s, 3H, CH$_3$), 6.21 (s, 1H, Cp-H), 6.71 (d, J=8.4 Hz, 1H, C$_6$H$_4$), 6.93 (d, J=8.4 Hz, 1H, C$_6$H$_4$), 6.95 (t, J=8.4 Hz, 1H, C$_6$H$_4$), 7.10 (t, J=8.4 Hz, 1H, C$_6$H$_4$) ppm Comparative Example 8

Dimethylsilyl(t-butylamido)(tetramethylcyclopentadienyl)titanium dichloride

Dimethylsilyl(t-butylamido) (tetramethylcyclopentadienyl) titaniumdichloride manufactured by Boulder Scientific was used as received.

Ethylene Copolymerization

Example 30

Copolymerization of ethylene and 1-octene at a high pressure

To a 2 L-autoclave, a hexane (1.0 L) solvent and 1-octene (144 mL) were put, and the reactor temperature was preliminarily heated to 90° C. Into a 25 mL-catalyst reservoir, a titanium compound (5.0 mmol) treated with triisobutylaluminum (125 mmol) and trityl tetrakis(pentafluorophenyl)borate (25 mmol) cocatalyst were sequentially charged. Then, to the reactor of the autoclave, an ethylene pressure (13 bar) was applied, and the catalyst composition was injected to the reactor using a high-pressure argon gas to perform a copolymerization reaction for 10 minutes. Thereafter, the remaining ethylene gas was discharged, and a polymer solution was added to an excessive amount of ethanol to derive precipitation. The precipitated polymer was washed with ethanol and acetone, each washing being performed twice or three times, and then dried in a vacuum oven at 80° C. for 12 hours or longer. The titanium transition metal compounds used for copolymerization, the measured polymer molecular weights and physical properties are shown in the following Table 1.

TABLE 1

Result of copolymerization of ethylene and 1-octene

| Complex compound used | Activity (Kg/mmol-Ti hr) | Mw | PDI | Melting point(° C.) |
|---|---|---|---|---|
| Example 20 | 80.60 | 218470 | 3.58 | 79.5/112.9 |
| Example 21 | 72.84 | 314161 | 3.85 | 75.3/112.8 |
| Example 22 | 96.48 | 348414 | 3.74 | 71.8/106.4 |
| Example 23 | 73.04 | 333706 | 3.34 | 73.4/105.6 |
| Example 24 | 80.57 | 287216 | 3.72 | 65.0/106.4 |
| Example 29 | 167.19 | 389418 | 4.15 | 79.3/105.8 |
| Comparative Example 4 | 24.46 | 686076 | 4.75 | 70.10 |
| Comparative Example 7 | 34.20 | 386410 | 4.37 | 77.35 |
| Comparative Example 8 | 191.61 | 251512 | 4.01 | 95.5 |

As shown in Table 1, the copolymers prepared by using the transition metal compounds in Examples of the present invention showed double composition distributions indicating two melting points, while the copolymers prepared by using the transition metal compounds in Comparative Examples of the present invention showed only one melting point. In particular, it can be seen that in the present invention, it is advantageous that the substituent linked to a nitrogen atom in the transition metal compound is an aliphatic ring to prepare a polyolefin having a double composition distribution.

The invention claimed is:

1. A catalyst composition comprising:
   a) a transition metal compound of the Formula 2 below;

Formula 2

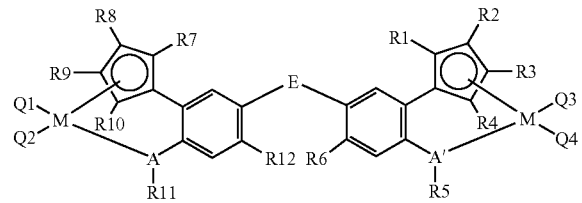

wherein

R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;

R5 and R11 is an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom;

E is a covalent bridging group for bridging two phenylene rings, which is an epoxy group; an epithio group; a carbonyl group; a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms;

Q1 to Q4 are each independently a halogen radical; an alkylamido radical having 1 to 20 carbon atoms; an arylamido radical; an alkyl radical having 1 to 20 carbon atoms; an alkenyl radical; an aryl radical; an alkylaryl radical; an arylalkyl radical; or an alkylidene radical having 1 to 20 carbon atoms; and M is a Group 4 transition metal;

and b) at least one cocatalyst compound selected from the group consisting of the compounds represented by the Formulae 3 to 5 below:

—[Al(R31)-O]$_a$—  Formula 3 wherein R31's are each independently a halogen radical; a hydrocarbyl radical having 1 to 20 carbon atoms; or a halogen-substituted hydrocarbyl radical having 1 to 20 carbon atoms; and a is an integer of 2 or more;

J(R32)$_3$  Formula 4 wherein J is aluminum or boron; R32's are each independently a halogen radical; a hydrocarbyl radical having 1 to 20 carbon atoms; or a halogen-substituted hydrocarbyl radical having 1 to 20 carbon atoms; and

[L-H]$^+$[Z(R33)$_4$]$^-$ or [L]$^+$[Z(R33)$_4$]$^-$  Formula 5 wherein L is a neutral or cationic Lewis acid; H is a hydrogen atom; Z is a Group 13 element; R33's are each independently an alkyl or aryl radical having 6 to 20 carbon atoms, having at least one hydrogen atom substituted with halogen; a hydrocarbyl radical having 1 to 20 carbon atoms; or an alkoxy or phenoxy radical.

2. The catalyst composition according to claim 1, wherein the compound of the Formula 2 is a compound of the Formula 7 below:

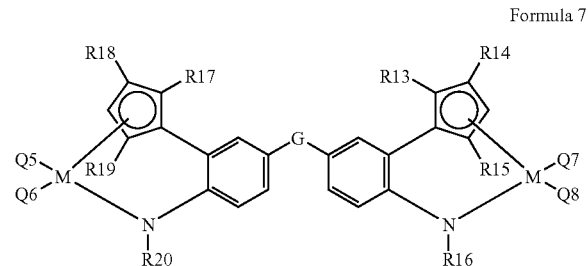

Formula 7 wherein

R13 to R15, and R17 to R19 are each independently a hydrogen atom; an alkyl radical having 1 to 20 carbon atoms; an aryl radical; or a silyl radical;

R16 and R20 are each independently an alkyl radical having 1 to 20 carbon atoms; a cycloalkyl radical having 3 to 20 carbon atoms; an aryl radical; a silyl radical; an alkenyl radical having to 20 carbon atoms; an alkylaryl radical; or an arylalkyl radical;

Q5 to Q8 are each independently a halogen radical; an alkylamido radical having 1 to 20 carbon atoms; an arylamido radical; or an alkyl radical having 1 to 20 carbon atoms;

G is an epoxy group; an epithio group; a carbonyl group; a heterohydrocarbylene group having 1 to 60 carbon atoms, substituted with a substituent containing an oxygen or nitrogen atom; or —C(R21)$_2$- (wherein R21 is hydrogen, or alkyl having 1 to 20 carbon atoms; aryl; silyl; alkenyl having 2 to 20 carbon atoms; alkylaryl; or arylalkyl); or a metalloid radical of a Group 14 metal substituted with hydrocarbyl; and M is a Group 4 transition metal.

3. The catalyst composition according to claim 2, wherein the compound of the Formula 7 is a compound of the Formula 8 below:

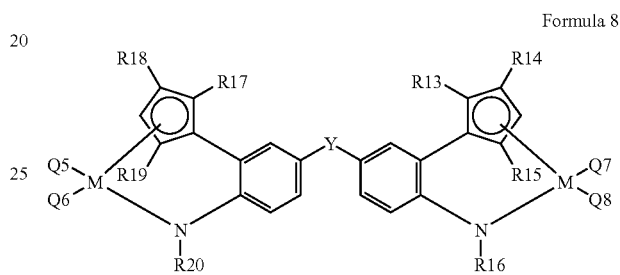

Formula 8 wherein

Y is —CH$_2$—, —C(CH$_3$)$_2$—, —C(=O)—, —C(=NR22)-, —O— or —S—, wherein R22 is a hydrogen atom; an alkyl radical having 1 to 20 carbon atoms; an aryl radical; a silyl radical; an alkenyl radical having 2 to 20 carbon atoms; an alkylaryl radical; or an arylalkyl radical;

R13 to R20, Q5 to Q8, and M each have the same meanings as defined in the Formula 7.

4. The catalyst composition according to claim 1, wherein the compound of the Formula 2 is a compound of the following Formula 9 below:

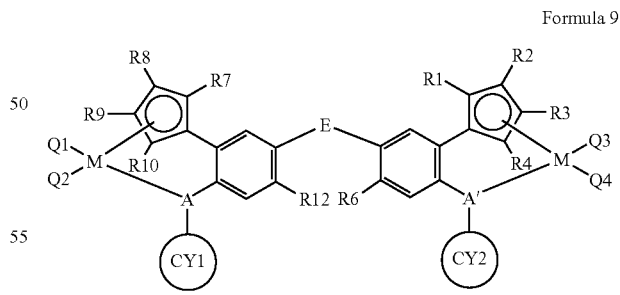

Formula 9 wherein

R1 to R4, R6 to R10, R12, Q1 to Q4, A, A', E and M each have the same meanings as defined in the formula 2, and CY1 and CY2 are each independently an aliphatic ring having 5 to 20 carbon atoms.

5. The catalyst composition according to claim 4, wherein the compound of the formula 9 is a compound of the Formula 10 below:

Formula 10

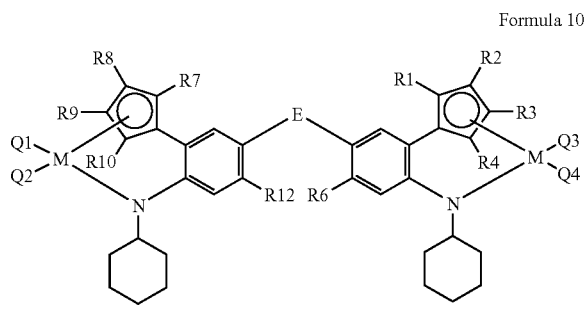

wherein R1 to R4, R6 to R10, R12, Q1 to Q4, E and M each have the same meanings as defined in the formula 9.

6. A method for preparing a catalyst composition, comprising the steps of: a) contacting a transition metal compound of the Formula 2 below, with a compound represented by the Formula 3 or 4 below to obtain a mixture; and b) adding a compound represented by the Formula 5 below to the mixture obtained in the a) step: wherein
Formula 2 is

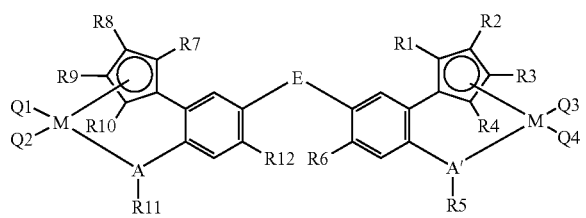

wherein
R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;
R5 and R11 is an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;
R6 and R12 are each independently a hydrogen atom; a halogen radical; an alkyl radical having 1 to 20 carbon atoms; or an aryl radical, or R6 and R12 may be bonded to each other;
A and A' are each independently a nitrogen or phosphorous atom;
E is a covalent bridging group for bridging two phenylene rings, which is an epoxy group; an epithio group; a carbonyl group; a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms;
Q1 to Q4 are each independently a halogen radical; an alkylamido radical having 1 to 20 carbon atoms; an arylamido radical; an alkyl radical having 1 to 20 carbon atoms; an alkenyl radical; an aryl radical; an alkylaryl radical; an arylalkyl radical; or an alkylidene radical having 1 to 20 carbon atoms; and
M is a Group 4 transition metal;
Formula 3 is —[Al(R31)-O]$_a$— wherein R31's are each independently a halogen radical; a hydrocarbyl radical having 1 to 20 carbon atoms; or a halogen-substituted hydrocarbyl radical having 1 to 20 carbon atoms; and
a is an integer of 2 or more;
Formula 4 is

J(R32)$_3$ wherein J is aluminum or boron; R32's are each independently a halogen radical; a hydrocarbyl radical having 1 to 20 carbon atoms;
or a halogen-substituted hydrocarbyl radical having 1 to 20 carbon atoms; and
Formula 5 is

[L-H]$^+$[Z(R33)$_4$]$^-$ or [L]$^+$[Z(R33)$_4$]$^-$ wherein L is a neutral or cationic Lewis acid; H is a hydrogen atom; Z is a Group 13 element; R33's are each independently an alkyl or aryl radical having 6 to 20 carbon atoms, having at least one hydrogen atom substituted with halogen; a hydrocarbyl radical having 1 to 20 carbon atoms; or an alkoxy or phenoxy radical.

7. The method for preparing the catalyst composition according to claim 6, wherein the molar ratio of the compound represented by the Formula 3 or 4 to the transition metal compound is 1:2 to 1:5,000, and the molar ratio of the compound represented by the Formula 5 to the transition metal compound is 1:1 to 1:25.

8. A method for preparing a catalyst composition, comprising a step of contacting a transition metal compound of the Formula 2 below, with a compound represented by the Formula 3 below to obtain a mixture:
wherein Formula 2 is

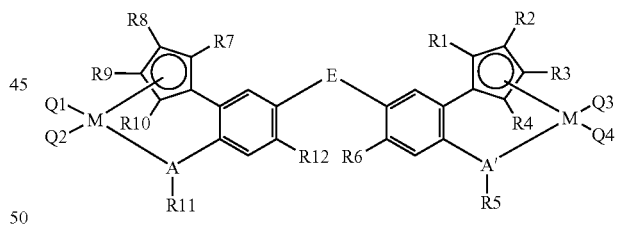

wherein
R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;
R5 and R11 is an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom;

E is a covalent bridging group for bridging two phenylene rings, which is an epoxy group; an epithio group; a carbonyl group;

a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms;

Q1 to Q4 are each independently a halogen radical; an alkylamido radical having 1 to 20 carbon atoms; an arylamido radical; an alkyl radical having 1 to 20 carbon atoms; an alkenyl radical; an aryl radical; an alkylaryl radical; an arylalkyl radical; or an alkylidene radical having 1 to 20 carbon atoms; and M is a Group 4 transition metal; and Formula 3 is —[Al(R31)-O]$_a$— wherein R31's are each independently a halogen radical; a hydrocarbyl radical having 1 to 20 carbon atoms; or a halogen-substituted hydrocarbyl radical having 1 to 20 carbon atoms; and a is an integer of 2 or more.

9. The method for preparing the catalyst composition according to claim 8, wherein the molar ratio of the compound represented by the Formula 3 to the transition metal compound is 1:10 to 1:10,000.

10. A method for preparing a catalyst composition, comprising a step of contacting at least one transition metal compound selected from the group consisting of a transition metal compound of the Formula 2 below, with a compound represented by the Formula 5 below to obtain a mixture:

wherein Formula 2 is

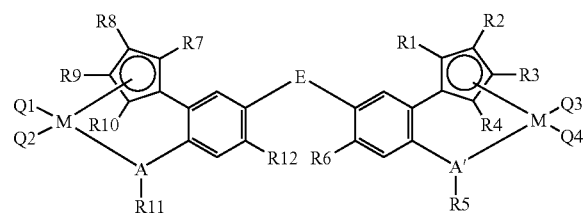

wherein R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;

R5 and R11 is an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom;

E is a covalent bridging group for bridging two phenylene rings, which is an epoxy group; an epithio group; a carbonyl group;

a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms;

Q1 to Q4 are each independently a halogen radical; an alkylamido radical having 1 to 20 carbon atoms; an arylamido radical; an alkyl radical having 1 to 20 carbon atoms; an alkenyl radical; an aryl radical; an alkylaryl radical; an arylalkyl radical; or an alkylidene radical having 1 to 20 carbon atoms; and M is a Group 4 transition metal; and Formula 5 is

[L-H]$^+$[Z(R33)$_4$]$^-$ or [L]$^+$[Z(R33)$_4$]$^-$ wherein L is a neutral or cationic Lewis acid; H is a hydrogen atom; Z is a Group 13 element; R33's are each independently an alkyl or aryl radical having 6 to 20 carbon atoms, having at least one hydrogen atom substituted with halogen; a hydrocarbyl radical having 1 to 20 carbon atoms; or an alkoxy or phenoxy radical.

11. The method for preparing the catalyst composition according to claim 10, wherein the molar ratio of the compound represented by the Formula 5 to the transition metal compound is 1:1 to 1:25.

12. A method for preparing a polyolefin having a double composition distribution, comprising a step of contacting the catalyst composition according to claim 1 and an olefin monomer.

13. The method for preparing a polyolefin according to claim 12, wherein the olefin monomer include one, or two or more selected from ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, and 3-chloromethylstyrene.

* * * * *

UNITED STATES PATENT AND TRADEMARK OFFICE
CERTIFICATE OF CORRECTION

PATENT NO.        : 7,807,762 B2
APPLICATION NO.   : 12/087216
DATED             : October 5, 2010
INVENTOR(S)       : Lee et al.

It is certified that error appears in the above-identified patent and that said Letters Patent is hereby corrected as shown below:

In the Specification
　　Column 1, line 34, "1990's" should read --1990s--.
　　Column 1, line 38, add "," after catalysts.
　　Column 1, line 41, "yield" should read --yields--.
　　Column 1, line 54, "followings" should read --following--.
　　Column 2, line 41, "is" should read --are--.
　　Column 3, line 39, "is" should read --are--.
　　Column 3, line 40, "it exhibits" should read --they exhibit--.
　　Column 3, line 46, "were" should read --was--.
　　Column 3, line 55, "describes" should read --describe--.
　　Column 3, line 61, "describes" should read --describe--.
　　Column 5, line 39, "R11 is" should read --R11 are--.
　　Column 5, line 66, "R31's" should read --R31s--.
　　Column 6, line 6, "R32's" should read --R32s--.
　　Column 6, line 13, "R33's" should read --R33s--.
　　Column 6, line 62, "that it represented" should read --that it is represented--.
　　Column 7, line 17, "provide" should read --provides--.
　　Column 7, line 44, "affect with each" should read --affect each--.
　　Column 7, line 55, "to a the" should read --to the--.
　　Column 11, lines 34-35, "it would not to particularly use" should read --is not particularly
used--.
　　Column 11, line 55, delete "," between composition and comprising.
　　Column 13, line 66, "invention, as the" should read --invention, the--.
　　Column 14, line 39, "is" should read --are--.

In the Claims
　　Column 28, line 54, Claim 1, "R11 is" should read --R11 are--.
　　Column 29, line 20, Claim 1, "R31's are" should read --R31 is--.
　　Column 29, line 28, Claim 1, "R32's are" should read --R32 is--.

Signed and Sealed this
Twenty-fourth Day of December, 2013

Margaret A. Focarino
*Commissioner for Patents of the United States Patent and Trademark Office*

CERTIFICATE OF CORRECTION (continued)
U.S. Pat. No. 7,807,762 B2

Column 29, line 34, Claim 1, "R33's are" should read --R33 is--.

Column 29, line 64, Claim 2, "having to 20 carbon" should read --having 2 to 20 carbon--.

Column 30, lines 43-44, Claim 4, "of the following Formula 9 below" should read --of the Formula--.

Column 30, line 66, Claim 5, "formula 9" should read --Formula 9--.

Column 31, line 16, Claim 5, "formula 9" should read --Formula 9--.

Column 31, line 46, Claim 6, "is" should read --are--.